(12) United States Patent
Tsukada et al.

(10) Patent No.: US 7,980,697 B2
(45) Date of Patent: Jul. 19, 2011

(54) FUNDUS OCULI OBSERVATION DEVICE AND OPHTHALMIC IMAGE DISPLAY DEVICE

(75) Inventors: Hisashi Tsukada, Tokyo (JP); Yasufumi Fukuma, Fort Lee, NJ (US)

(73) Assignee: Kabushiki Kaisha Topcon, Itabashi-k (JP)

( * ) Notice: Subject to any disclaimer, the term of this patent is extended or adjusted under 35 U.S.C. 154(b) by 326 days.

(21) Appl. No.: 12/051,981

(22) Filed: Mar. 20, 2008

(65) Prior Publication Data
US 2009/0190092 A1  Jul. 30, 2009

(30) Foreign Application Priority Data
Mar. 23, 2007  (JP) ................................ 2007-077685

(51) Int. Cl.
*A61B 3/14* (2006.01)
*A61B 3/10* (2006.01)

(52) U.S. Cl. ......... 351/208; 351/206; 351/210; 351/221
(58) Field of Classification Search .................. 351/206, 351/208, 200, 204, 205, 210, 214, 221
See application file for complete search history.

(56) References Cited

U.S. PATENT DOCUMENTS

| 5,537,162 | A | 7/1996 | Hellmuth et al. |
| 2004/0036838 | A1 | 2/2004 | Podoleanu et al. |
| 2006/0114411 | A1 | 6/2006 | Wei et al. |
| 2006/0164653 | A1 | 7/2006 | Everett et al. |

FOREIGN PATENT DOCUMENTS

| EP | 1836952 | 9/2007 |
| EP | 1908397 | 4/2008 |
| EP | 1952755 | 8/2008 |
| JP | 11-253403 | 9/1999 |
| JP | 2003-000543 A | 1/2003 |
| JP | 2004-350849 A | 12/2004 |
| JP | 2005-241464 A | 9/2005 |
| JP | 2008-073099 A | 4/2008 |
| WO | WO-2006/077045 | 7/2006 |

OTHER PUBLICATIONS

Motion Estimation of Ocular Fundus Images by Petrig, B.L.; Bigun, J.; Curchod, M.G. In Image Processing, 1996. Proceedings., International Conference on vol. 3, Issue 16-19, 1996, p. 691-694 Digital Object Identifier 10.1109/ICIP.1996.560756.

(Continued)

*Primary Examiner* — Jack Dinh
(74) *Attorney, Agent, or Firm* — Edwards Angell Palmer & Dodge LLP

(57) ABSTRACT

A fundus oculi observation device comprises: a first image forming part configured to form a 2-dimensional image of a surface of a fundus oculi of an eye; a second image forming part configured to form a tomographic image having a cross-sectional position in a measurement region of the fundus oculi corresponding to a partial region of the 2-dimensional image; a display; a storage configured to store imaging condition information including characteristic information showing a characteristic of the eye; and a controller configured to match display sizes of the formed 2-dimensional image and a measurement range image showing a range of the measurement region with each other, based on the stored imaging condition information, and cause the display to display the 2-dimensional image and the measurement range image whose display sizes are matched.

7 Claims, 16 Drawing Sheets

OTHER PUBLICATIONS

Eye Movement Analysis system Using Fundus Images by Kawai, Hideo; Tamura, Shinichi; Kain, Kazutaka; Kariya, Kmoyo in Pattern Recognition, vol. 19, Issue 1 (Jan./Feb. 1986), pp. 77-84, Pub. 1986, ISSN:0031-3203.

Eye movement Measurement with the Scanning Laser Ophthalmoscope by Ott, D. And Daunicht, W.J. (1992) in Clinical Vision Science (Clin. screws. Sci.) ISSN 0887-6169 Coden CVSCEX, 1992, vol. 7, No. 6 (27 ref.), p. 551-556.

Efficient Detection of Eye Movements in Video Image Sequences by Lakmann, R. in.

R. B. Rosen, "Simultaneous OCT/SLO/ICG System," Proc of SPIE, vol. 6079, Feb. 20, 2006, pp. 60790A-1 through 60790A-6.

European Search Report mailed Oct. 23, 2008, issued on the corresponding European patent application No. 08005209.5.

NEDO Workshop, "Seeing (examining) inside the body form the 'window' of the human body, the fundus oculi"—Development of an ultra early diagnostic device for lifestyle-related diseases using the latest optical technologies, Apr. 25, 2005.

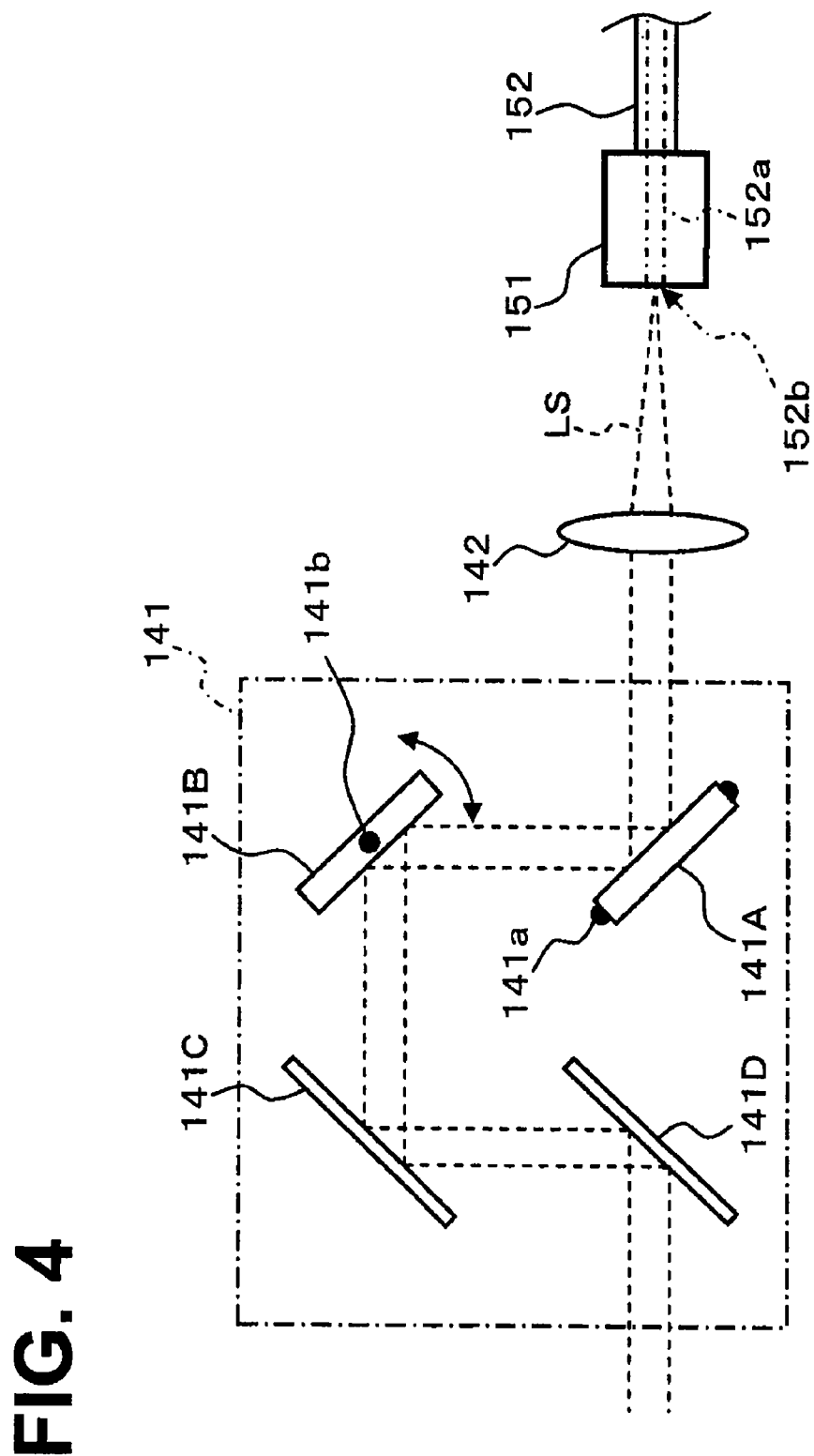

FUNDUS OCULI OBSERVATION DEVICE AND OPHTHALMIC IMAGE DISPLAY DEVICE

BACKGROUND OF THE INVENTION

1. Field of the Invention

The present invention relates to a fundus oculi observation device and an ophthalmic image display device that are used for observation of a fundus oculi of an eye.

2. Description of the Related Art

As a fundus oculi observation device, a retinal camera has been widely used conventionally. FIG. 15 shows an example of the appearance of a conventional and general retinal camera. FIG. 16 shows an example of the configuration of an optical system internally accommodated in the retinal camera (refer to Japanese Unexamined Patent Application Publication JP-A 2004-350849, for example). First, referring to FIG. 15, the appearance of a conventional retinal camera 1000 will be described. The retinal camera 1000 is provided with a platform 3 mounted on a base 2 so as to be slidable in the front and rear, right and left directions (horizontal directions). On this platform 3, an operation panel and a control lever 4 for an examiner to perform various operations are mounted.

The examiner can 3-dimensionally move the platform 3 on the base 2 by operating the control lever 4. On the top of the control lever 4, an operation button 4a pressed down at the time of capturing a fundus oculi is mounted.

On the base 2, a post 5 is mounted standing upward. This post 5 is provided with a jaw rest 6 where a jaw of a subject is rested, and an external fixation lamp 7 serving as a light source for fixing an eye E.

On the platform 3, a main body part 8 is placed for accommodating various optical systems and control systems of the retinal camera 1000. The control system may be placed, for example, inside the base 2 or the platform 3, or in an external device such as a computer connected to the retinal camera 1000.

On the eye E side of the main body part 8 (i.e., on the left side on the sheet of FIG. 15), an objective lens part 8a placed facing the eye E is disposed. Moreover, on the examiner's side (i.e., on the right side on the sheet of FIG. 15), an eyepiece part 8b for observing the fundus oculi of the eye E with naked eyes is disposed.

Furthermore, to the main body part 8, a still camera 9 for producing a still image of the fundus oculi of the eye E and an imaging device 10 such as a TV camera for producing a still image or moving image of the fundus oculi are disposed. The still camera 9 and the imaging device 10 are formed so as to be removable from the main body part 8.

As the still camera 9, in accordance with various conditions such as the purpose of an examination and a method of saving a captured image, a digital camera equipped with an imaging device such as a CCD (charge coupled device) and a CMOS (complementary metal oxide semiconductor), a film camera, an instant camera and the like may be interchangeably used as necessary. The main body part 8 is provided with a mounting part 8c for interchangeably mounting the still camera 9.

In a case where the still camera 9 and the imaging device 10 are of digital imaging type, it is possible to send image data of fundus oculi images captured by these components to a computer or the like connected to the retinal camera 1000, and observe by displaying the fundus oculi images on a display. Further, it is possible to send the image data to an image recording device connected to the retinal camera 1000 and create a database, and use it as, for example, electronic data for creating an electronic medical record.

Further, on the examiner's side of the main body part 8, a touch panel monitor 11 is disposed. On this touch panel monitor 11, a fundus oculi image of the eye E formed based on video signals outputted from the (digital-type) still camera 9 or imaging device 10 is displayed. Moreover, on the touch panel monitor 11, an x-y coordinate system taking the center of a screen as the origin is displayed superimposed on the fundus oculi image. When the examiner touches the screen, coordinate values corresponding to a touched position are displayed.

Next, referring to FIG. 16, the configuration of the optical system of the retinal camera 1000 will be described. The retinal camera 1000 is provided with an illumination optical system 100 that illuminates a fundus oculi Ef of the eye E, and an imaging optical system 120 that guides the illumination light reflected by the fundus oculi to the eyepiece part 8b, the still camera 9 and the imaging device 10.

The illumination optical system 100 comprises: an observation light source 101; a condenser lens 102; an imaging light source 103; a condenser lens 104; exciter filters 105 and 106; a ring transparent plate 107; a mirror 108; an LCD (Liquid Crystal Display) 109; an illumination diaphragm 110; a relay lens 111; an aperture mirror 112; and an objective lens 113.

The observation light source 101 is composed of, for example, a halogen lamp, and emits continuous light for fundus oculi observation. The condenser lens 102 is an optical element for converging the continuous light (observation illumination light) emitted by the observation light source 101 and almost evenly applying the observation illumination light to the fundus oculi Ef.

The imaging light source 103 is composed of, for example, a xenon lamp, and is flashed at the time of imaging of the fundus oculi Ef. The condenser lens 104 is an optical element for converging the flash light (imaging illumination light) emitted by the imaging light source 103 and evenly applying the imaging illumination light to the fundus oculi Ef.

The exciter filters 105 and 106 are filters used at the time of fluorography of an image of the fundus oculi Ef. The exciter filters 105 and 106 can be respectively inserted into and removed from an optical path by a drive mechanism (not illustrated) such as a solenoid. The exciter filter 105 is placed on the optical path at the time of FAG (fluorescein angiography). The exciter filter 106 is placed on the optical path at the time of ICG (indocyanine green angiography). At the time of color-imaging, both the exciter filters 105 and 106 are retracted from the optical path.

The ring transparent plate 107 is placed in a conjugating position with a pupil of the eye E, and is provided with a ring transparent part 107a taking the optical axis of the illumination optical system 100 as the center. The mirror 108 reflects the illumination light emitted by the observation light source 101 or imaging light source 103, in a direction of the optical axis of the imaging optical system 120. The LCD 109 displays a fixation target (not illustrated) for fixing the eye E.

The illumination diaphragm 110 is a diaphragm member to shut out part of the illumination light in order to prevent flare and the like. This illumination diaphragm 110 is configured so as to be movable in the optical axis direction of the illumination optical system 100, and is thus capable of changing an illumination region of the fundus oculi Ef.

The aperture mirror 112 is an optical element that combines the optical axis of the illumination optical system 100 and the optical axis of the imaging optical system 120. In the center region of the aperture mirror 112, an aperture 112a is opened. The optical axis of the illumination optical system 100 and the optical axis of the imaging optical system 120 cross each other at a substantially central position of the aperture 112a. The objective lens 113 is installed in the objective lens part 8a of the main body part 8.

The illumination optical system 100 having such a configuration illuminates the fundus oculi Ef in the following manner. First, at the time of fundus oculi observation, the observation light source 101 is turned on and an observation illumination light is emitted. This observation illumination light is applied to the ring transparent plate 107 through the condenser lenses 102 and 104 (the exciter filters 105 and 106 are retracted from the optical path). The light passed through the ring transparent part 107a of the ring transparent plate 107 is reflected by the mirror 108 and, after passing through the LCD 109, the illumination diaphragm 110 and the relay lens 111, is reflected by the aperture mirror 112. The observation illumination light reflected by the aperture mirror 112 travels in the optical axis direction of the imaging optical system 120, and is converged by the objective lens 113, thereby entering the eye E and illuminate the fundus oculi Ef.

At this moment, since the ring transparent plate 107 is placed in a conjugating position with the pupil of the eye E, a ring-shaped image of the observation illumination light entering the eye E is formed on the pupil. The entering fundus oculi reflection light of the entered observation illumination light is emitted from the eye E through a central dark part of the ring-shaped image on the pupil. Thus, the observation illumination light entering the eye E is prevented from affecting the fundus oculi reflection light of the observation illumination light.

On the other hand, at the time of imaging of the fundus oculi Ef, flush light is emitted from the imaging light source 103, and the imaging illumination light is applied to the fundus oculi Ef through the same path. In the case of fluorography, either the exciter filter 105 or the exciter filter 106 is selectively placed on the optical path, depending on whether FAG imaging or ICG imaging is carried out.

Next, the imaging optical system 120 will be described. The imaging optical system 120 comprises: an objective lens 113; an aperture mirror 112 (an aperture 112a thereof); an imaging diaphragm 121; barrier filters 122 and 123; a variable magnifying lens 124; a relay lens 125; an imaging lens 126; a quick return mirror 127; and an imaging media 9a. Herein, the imaging media 9a is an imaging media (a CCD, camera film, instant film or the like) for the still camera 9.

The fundus oculi reflection light of the illumination light exiting from the eye E through the central dark part of the ring-shaped image formed on the pupil enters the imaging diaphragm 121 through the aperture 112a of the aperture mirror 112. The aperture mirror 112 reflects cornea reflection light of the illumination light, and acts so as not to mix the cornea reflection light into the fundus oculi reflection light entering the imaging diaphragm 121. Consequently, generation of flare in observation images and captured images is inhibited.

The imaging diaphragm 121 is a plate-shaped member having a plurality of circular light-transmitting parts of different sizes. The plurality of light-transmitting parts compose diaphragms with different diaphragm values (F values), and are placed alternatively on the optical path by a drive mechanism (not illustrated).

The barrier filters 122 and 123 can be inserted into and removed from the optical path by a drive mechanism (not illustrated) such as a solenoid. In FAG imaging, the barrier filter 122 is placed on the optical path, whereas in ICG imaging, the barrier filter 123 is placed on the optical path. Further, at the time of color-imaging, both the barrier filters 122 and 123 are retracted from the optical path.

The variable magnifying lens 124 is movable in the optical axis direction of the imaging optical system 120 by a drive mechanism (not illustrated). This makes it possible to change an observation magnifying ratio and an imaging magnifying ratio, and to focus images of the fundus oculi. The imaging lens 126 is a lens that focuses the fundus oculi reflection light from the eye E onto the imaging media 9a.

The quick return mirror 127 is disposed so as to be capable of being rotated around a rotary shaft 127a by a drive mechanism (not illustrated). In a case where imaging of the fundus oculi Ef is performed with the still camera 9, the fundus oculi reflection light is guided to the imaging media 9a by springing up the quick return mirror 127 that is obliquely mounted on the optical path. Meanwhile, in a case where imaging of the fundus oculi is performed with the imaging device 10, or in a case where observation of the fundus oculi is performed with the naked eye of the examiner, the quick return mirror 127 is obliquely mounted on the optical path to upwardly reflect the fundus oculi reflection light.

The imaging optical system 120 is further provided with, for guiding the fundus oculi reflection light reflected by the quick return mirror 127, a field lens 128, a switching mirror 129, an eyepiece 130, a relay lens 131, a reflection mirror 132, an imaging lens 133, and an image pick-up element 10a. The image pick-up element 10a is an image pick-up element such as a CCD installed in the imaging device 10. On the touch panel monitor 11, a fundus oculi image Ef imaged by the image pick-up element 10a is displayed.

The switching mirror 129 is rotatable around a rotary shaft 129a in the same manner as the quick return mirror 127. This switching mirror 129 is obliquely disposed on the optical path during observation with the naked eye, thereby reflecting and guiding the fundus oculi reflection light to the eyepiece 130.

Further, at the time of capture of a fundus oculi image by using the imaging device 10, the switching mirror 129 is retracted from the optical path, and the fundus oculi reflection light is guided toward the image pick-up element 10a. In this case, the fundus oculi reflection light is passed through the relay lens 131 and reflected by the mirror 132, whereby an image is formed in the image pick-up element 10a by the imaging lens 133.

This retinal camera 1000 is a fundus oculi observation device used for observing the state of the surface of the fundus oculi Ef, namely, the state of the retina. In other words, the retinal camera 1000 is a device for acquiring a 2-dimensional fundus oculi image when the fundus oculi Ef is seen from the cornea of the eye E. On the other hand, organs such as the choroidea and the sclera exist in the deeper layers of the retina. There has been a demand for a technique for observing the state of these organs, and in recent years, there has been progress in the practical utilization of devices for observing these deeper layer organs (refer to Japanese Unexamined Patent Application Publications Nos. JP-A 2003-000543 and JP-A 2005-241464).

Each of the devices disclosed in JP-A 2003-000543 and JP-A 2005-241464 is an optical image measurement device to which a so-called OCT (Optical Coherence Tomography) technology is applied (referred to as an optical coherence topography device, or the like). Such an optical image measurement device is a device that splits low-coherence light into two, guides one (signal light) of the lights to the fundus oculi and the other (reference light) to a given reference object, and detects and analyzes interference light obtained by superimposing the signal light passed through the fundus oculi and the reference light reflected by the reference object, thereby forming tomographic images of the surface and deep layer tissue of the fundus oculi or 3-dimensional images of the fundus oculi. Here, the optical image measurement device disclosed in JP-A 2003-000543 is generally called a Fourier domain OCT or the like.

The Fourier domain OCT is configured to scan with a signal light and apply the signal light to a fundus oculi, thereby forming a tomographic image having a depth-wise cross section along a scanning line. Such scan with a signal light is referred to as B-scan or the like (refer to, for example, NEDO Workshop "Seeing (examining) inside the body from the 'window' of the human body, the fundus oculi"—Development of an ultra early diagnostic device for lifestyle-related diseases using the latest optical technologies (held on Apr. 25, 2005), Internet <URL:http://www.nedo.go.jp/informations/koubo/170627_2/besshi3.pdf>).

Further, in the case of formation of a 3-dimensional image of a fundus oculi, 3-dimensional image data is generated by executing B-scan along a plurality of scanning lines and subjecting the plurality of tomographic images obtained thereby to an interpolation process. This 3-dimensional image data is referred to as volume data, voxel data or the like as in a medical image diagnosis device such as an X-ray CT device, and is image data with a form in which pixel data (data of brightness, contrasting density, color, etc., including a luminance value and a RGB value) is assigned to each of voxels arranged 3-dimensionally. The 3-dimensional image is displayed as a pseudo 3-dimensional image taken on a specific view direction obtained by rendering the volume data. In this specification, an image acquired by the optical image measurement device may be referred to as an OCT image.

In order to grasp the state (presence or absence of a disease) of a fundus oculi in detail, it is desirable to consider both an image acquired by a retinal camera and an image acquired by an optical image measurement device. This is because it is difficult to grasp the state of a deep layer organ such as choroidea and sclera in detail from only an image of a fundus oculi surface acquired by a retinal camera and it is hard to grasp the state of the fundus oculi surface throughout a wide range in detail from observation of only a fundus oculi image acquired by an optical image measurement device.

Further, in order to comprehensively determine the state of a fundus oculi, it is important to determine the disease state in consideration of both the state of the fundus oculi surface and the state of the deeper layer organs. In other words, to enhance the accuracy of determination of the disease state, it is desirable that more information is available as a reference, and it is also desirable that the reference information is available from multidimensional angles.

For this purpose, it is necessary to use a fundus oculi observation device that is capable of acquiring a fundus oculi image by a retinal camera and a fundus oculi image by an optical image measurement device. In particular, it is expected that a more detailed diagnosis can be achieved because it is possible, by using a device that is capable of capturing both the fundus oculi images simultaneously, to observe the state of the fundus oculi with one of the fundus oculi images during capture of the other fundus oculi image.

In the case of displaying images by both a retinal camera and an optical image measurement device, it is desirable to show such information that makes it possible to grasp the positional relationship between both the images. As this information, for example, an image showing a measurement range (measurement range image) of an OCT image on a fundus oculi image by a retinal camera will be usable. As the measurement range image, it is possible to use an image showing a range with a specific size (for example, an image like a frame surrounding a range of several mm×several mm approximately).

In the case of displaying such a measurement range image, it is necessary, in order to show the positional relationship between both the images with high accuracy, to match the display sizes of the fundus oculi image and the measurement range image in accordance with the characteristic of each eye.

The characteristic of an eye affecting the display size is, for example, an axial length. Each eye has an individual axial length. For example, an eye of axial myopia has a longer axial length than a healthy eye, and an eye of axial hyperopia has a shorter axial length than a healthy eye.

In a conventional fundus oculi observation device, it is impossible to match the display sizes of a fundus oculi image and a measurement range image, and it is impossible to show the positional relationship between an image by a retinal camera and an OCT image with high accuracy.

SUMMARY OF THE INVENTION

The present invention has been devised in consideration of the abovementioned condition, and an object of the present invention is to provide a fundus oculi observation device and an ophthalmic image display device that are capable of showing the positional relationship between a 2-dimensional image of a fundus oculi surface and an OCT image with high accuracy.

In order to achieve the aforementioned object, in a first aspect of the present invention, a fundus oculi observation device comprises: a first image forming part configured to form a 2-dimensional image of a surface of a fundus oculi of an eye; a second image forming part configured to form a tomographic image having a cross-sectional position in a measurement region of the fundus oculi corresponding to a partial region of the 2-dimensional image; a display; a storage configured to store imaging condition information including characteristic information showing a characteristic of the eye; and a controller configured to match display sizes of the formed 2-dimensional image and a measurement range image showing a range of the measurement region with each other, based on the stored imaging condition information, and cause the display to display the 2-dimensional image and the measurement range image whose display sizes are matched.

In a second aspect of the present invention, an ophthalmic image display device comprises: a display configured to display a 2-dimensional image of a surface of a fundus oculi of an eye and a tomographic image having a cross-sectional position in a measurement region of the fundus oculi corresponding to a partial region of the 2-dimensional image; a storage configured to store imaging condition information including characteristic information showing a characteristic of the eye; and a controller configured to match display sizes of the 2-dimensional image and a measurement range image showing a range of the measurement region with each other, based on the stored imaging condition information, and cause the display to display the 2-dimensional image and the measurement range image whose display sizes are matched.

According to the present invention, it is possible, based on imaging condition information that is stored in a storage, to display a 2-dimensional image of a fundus oculi surface and a measurement range image showing the range of a measurement region of a tomographic image (OCT image) in a state in which the display sizes are matched. Therefore, it is possible to show the positional relationship between the 2-dimensional image of the fundus oculi surface and the OCT image with high accuracy.

DESCRIPTION OF THE DRAWINGS

FIG. 4 is a schematic configuration diagram showing an example of the configuration of a scanning unit installed in a retinal camera unit in a preferred embodiment of the fundus oculi observation device according to the present invention.

FIG. 10A shows an example of the feature of scan of signal light when a fundus oculi is seen from the incident side of the signal light with respect to an eye. FIG. 10B shows one example of a feature of arrangement of scanning points on each scanning line.

DETAILED DESCRIPTION OF THE PREFERRED EMBODIMENT

Figure 1:
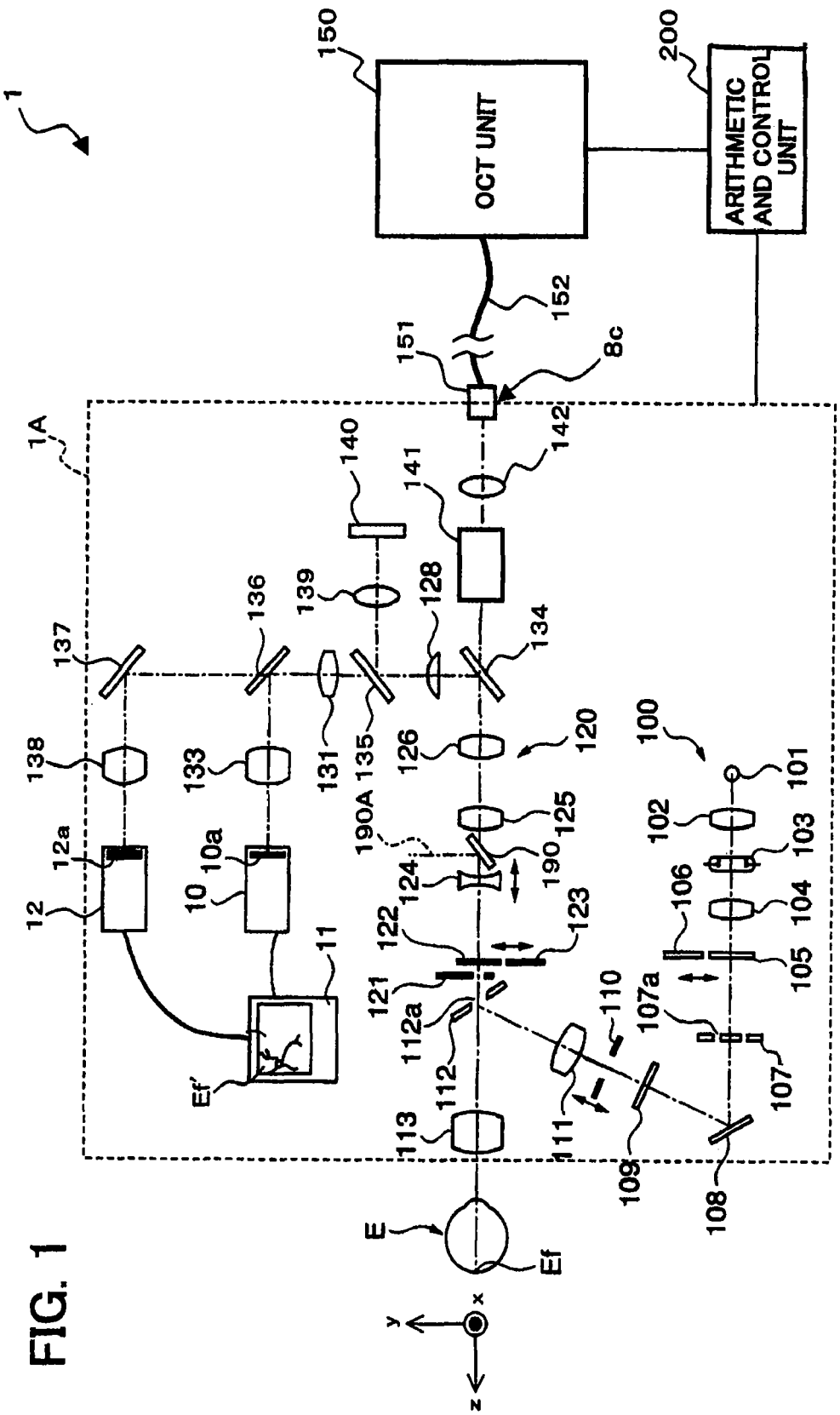
FIG. 1 is a schematic configuration diagram showing an example of the entire configuration in a preferred embodiment of the fundus oculi observation device according to the present invention.

An example of a preferred embodiment of a fundus oculi observation device and an ophthalmic image display device according to the present invention will be described in detail referring to the drawings. Here, the same components as the conventional ones will be described in FIGS. 15 and 16 will be denoted by the same reference symbols used therein.

[Entire Configuration of Fundus Oculi Observation Device]

A fundus oculi observation device 1 shown in FIG. 1 comprises an retinal camera unit 1A that functions in the same manner as a conventional retinal camera unit 1A, an OCT unit 150 that stores an optical system of an optical image measurement device (OCT device), and an arithmetic and control unit 200 that executes various kinds of processes such a an arithmetic process and a control process.

To the OCT unit 150, one end of a connection line 152 is attached. To the other end of the connection line 152, a connector part 151 is attached. This connector part 151 is mounted on a mounting part 8c shown in FIG. 15. Moreover, a conductive optical fiber runs through the inside of the connection line 152. Thus, the OCT unit 150 and the retinal camera unit 1A are optically connected via the connection line 152. The detailed configuration of the OCT unit 150 will be described later referring to FIG. 5.

[Configuration of Retinal Camera Unit]

First, the retinal camera unit 1A will be described with reference to FIGS. 1 to 4. The retinal camera unit 1A is a device configured to form a 2-dimensional image of the surface of a fundus oculi of an eye, based on optically obtained data (data detected by the imaging devices 10 and 12), and has almost the same appearance as the conventional retinal camera 1000 shown in FIG. 15. As in the conventional optical system shown in FIG. 16, the retinal camera unit 1A is provided with an illumination optical system 100 that illuminates the fundus oculi Ef of the eye E, and an imaging optical system 120 that guides the fundus oculi reflection light of the illumination light to the imaging device 10.

Although the details will be described later, the imaging device 10 in the imaging optical system 120 of the present embodiment detects the illumination light having a wavelength in the near-infrared region. Moreover, this imaging optical system 120 is further provided with the imaging device 12 for detecting the illumination light having a wavelength in the visible region. Moreover, this imaging optical system 120 guides a signal light coming from the OCT unit 150 to the fundus oculi Ef, and guides the signal light passed through the fundus oculi Ef to the OCT unit 150.

As in the conventional one, the illumination optical system 100 comprises: an observation light source 101; a condenser lens 102; an imaging light source 103; a condenser lens 104; exciter filters 105 and 106; a ring transparent plate 107; a mirror 108; an LCD (Liquid Crystal Display) 109; an illumination diaphragm 110; a relay lens 111; an aperture mirror 112; and an objective lens 113.

The observation light source 101 emits an illumination light having a wavelength of the visible region included in a range of, for example, about 400 nm thorough 700 nm. Moreover, the imaging light source 103 emits an illumination light having a wavelength of the near-infrared region included in a range of, for example, about 700 nm through 800 nm. The near-infrared light emitted from this imaging light source 103 is set so as to have a shorter wavelength than the light used by the OCT unit 150 (described later).

Further, the imaging optical system 120 comprises: an objective lens 113; an aperture mirror 112 (an aperture 112a thereof); an imaging diaphragm 121; barrier filters 122 and 123; a variable magnifying lens 124; a relay lens 125; an imaging lens 126; a dichroic mirror 134; a field lens 128; a half mirror 135; a relay lens 131; a dichroic mirror 136; an imaging lens 133; the imaging device 10 (image pick-up element 10a); a reflection mirror 137; an imaging lens 138; the imaging device 12 (image pick-up element 12a); a lens 139; and an LCD 140.

Figure 16:
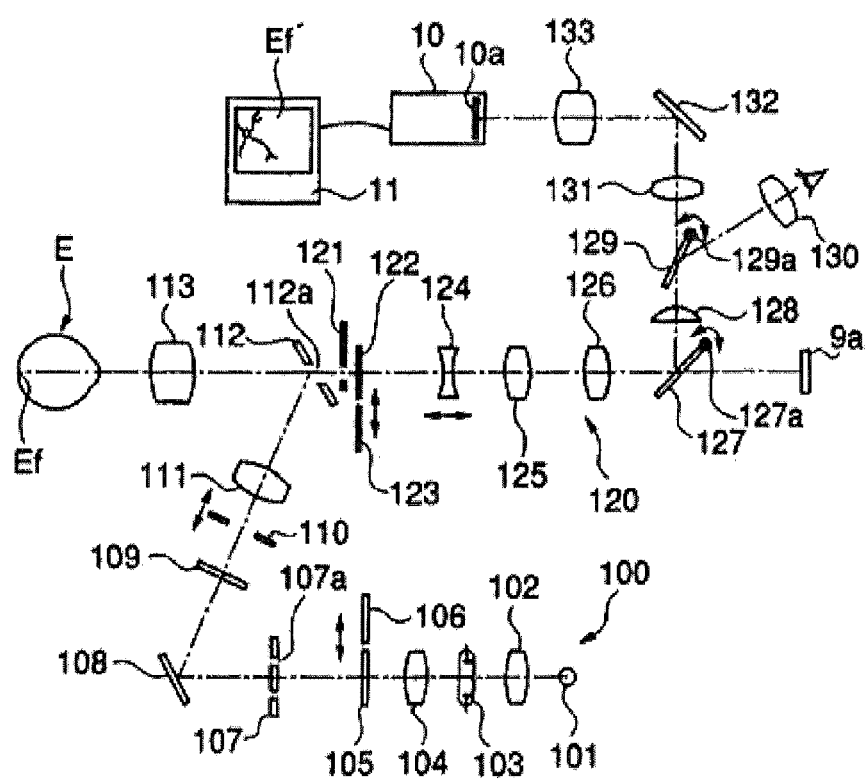
FIG. 16 is a schematic diagram showing an example of the internal configuration (optical system configuration) of a conventional fundus oculi observation device (retinal camera).

The imaging optical system 120 according to the present embodiment is different from the conventional imaging optical system 120 shown in FIG. 16 in that the dichroic mirror 134, the half mirror 135, the dichroic mirror 136, the reflection mirror 137, the imaging lens 138, the lens 139 and the LCD 140 are disposed.

The dichroic mirror 134 is configured to reflect the fundus oculi reflection light (having a wavelength included in a range of about 400 nm through 800 nm) of the illumination light from the illumination optical system 100, and transmit a signal light LS (having a wavelength included in a range of, for example, about 800 nm through 900 nm; described later) from the OCT unit 150.

Further, the dichroic mirror 136 is configured to transmit the illumination light having a wavelength of the visible region from the illumination optical system 100 (a visible light having a wavelength of about 400 nm through 700 nm emitted from the observation light source 101), and reflect the illumination light having a wavelength of the near-infrared region (a near-infrared light having a wavelength of about 700 nm through 800 nm emitted from the imaging light source 103).

On the LCD 140, a fixation target (internal fixation target) or the like for fixing the eye E is displayed. The light from this LCD 140 is reflected by the half mirror 135 after being converged by the lens 139, and is reflected by the dichroic mirror 136 through the field lens 128. Then, the light passes through the imaging lens 126, the relay lens 125, the variable magnifying lens 124, the aperture mirror 112 (aperture 112a thereof), the objective lens 113 and the like, and enters the eye E. Consequently, an internal fixation target or the like is projected in the fundus oculi Ef of the eye E.

The image pick-up element 10a is an image pick-up element such as a CCD and a CMOS installed in the imaging device 10 such as a TV camera, and is particularly used for detecting light having a wavelength of the near-infrared region (that is, the imaging device 10 is an infrared TV camera for detecting near-infrared light). The imaging device 10 outputs video signals as a result of detection of the near-infrared light. A touch panel monitor 11 displays a 2-dimensional image (a fundus oculi image Ef') of the surface of the fundus oculi Ef, based on the video signals. The video signals are sent to the arithmetic and control unit 200, and the fundus oculi image is displayed on the display (described later). At the time of imaging of the fundus oculi by the imaging device 10, for example, the illumination light emitted from the imaging light source 103 of the illumination optical system 100 and having a wavelength of the near-infrared region is used.

On the other hand, the image pick-up element 12a is an image pick-up element such as a CCD and a CMOS installed in the imaging device 12 such as a TV camera, and is particularly used for detecting light having a wavelength of the visible region (that is, the imaging device 12 is a TV camera for detecting visible light). The imaging device 12 outputs video signals as a result of detection of the visible light. The touch panel monitor 11 displays a 2-dimensional image (fundus oculi image Ef') of the surface of the fundus oculi Ef, based on the video signals. The video signals are sent to the arithmetic and control unit 200, and the fundus oculi image Ef' is displayed on the display (described later). At the time of imaging of the fundus oculi by the imaging device 12, for example, the illumination light emitted from the observation light source 101 of the illumination optical system 100 and having a wavelength of the visible region is used.

The imaging optical system 120 according to the present embodiment is provided with a scanning unit 141 and a lens 142. The scanning unit 141 includes a component for scanning at an application position of the fundus oculi Ef with light emitted from the OCT unit 150 (signal light LS; described later).

The lens 142 makes the signal light LS guided from the OCT unit 150 through the connection line 152 enter the scanning unit 141 in the form of a parallel light flux. Moreover, the lens 142 acts so as to converge the fundus oculi reflection light of the signal light LS passed through the scanning unit 141.

FIG. 4 shows one example of a specific configuration of the scanning unit 141. The scanning unit 141 comprises Galvano mirrors 141A and 141B, and reflection mirrors 141C and 141D.

The Galvano mirrors 141A and 141B are rotatable about rotary shafts 141a and 141b, respectively. The rotary shafts 141a and 141b are arranged so as to be orthogonal to each other. In FIG. 4, the rotary shaft 141a of the Galvano mirror 141A is arranged in parallel to the paper face of this figure, whereas the rotary shaft 141b of the Galvano mirror 141B is arranged so as to be orthogonal to the paper face of this figure. That is, the Galvano mirror 141B is formed so as to be rotatable in the directions indicated by an arrow pointing in both directions in FIG. 4, whereas the Galvano mirror 141A is formed so as to be rotatable in the directions orthogonal to the arrow pointing in both the directions. Consequently, the pair of Galvano mirrors 141A and 141B act so as to change the reflecting directions of the signal light LS to directions orthogonal to each other. Here, a rotation movement of each of the Galvano mirrors 141A and 141B is driven by a drive mechanism (refer to FIG. 7), which will be described later.

The signal lights LS reflected by the Galvano mirrors 141A and 141B are reflected by reflection mirrors 141C and 141D, thereby traveling in the same directions as having entered into the Galvano mirror 141A.

As described before, the conductive optical fiber 152a runs through the inside of the connection line 152, and an end face 152b of the optical fiber 152a is arranged facing the lens 142. The signal light LS emitted from this end face 152b travels while expanding its beam diameter toward the lens 142. The light is converged into a parallel light flux by this lens 142. On the contrary, the signal light LS passed through the fundus oculi Ef is converged toward the end face 152b by the lens 142, and guided to the optical fiber 152a.

A half mirror 190 is inclined on an optical path between the variable magnifying lens 124 and the relay lens 125. The half mirror 190 acts to combine the optical path of the alignment optical system 190A shown in FIG. 2A and the optical path of the imaging optical system 120 (imaging optical path). This alignment optical system 190A is an optical system for projecting, onto the eye E, an alignment bright point used in alignment of the optical system with the eye E.

This alignment bright point is used for both alignment of matching the top of the cornea of the eye E with the optical axes of the optical systems 100 and 120 (alignment in the x-y direction shown in FIG. 1) and alignment of a distance between the eye E and the optical systems 100 and 120 (the z direction in FIG. 1; working distance; a distance between (the top of) the cornea of the eye E and the objective lens 113) (e.g., refer to Japanese Unexamined Patent Application Publication JP-A 11-004808).

Figure 2A:
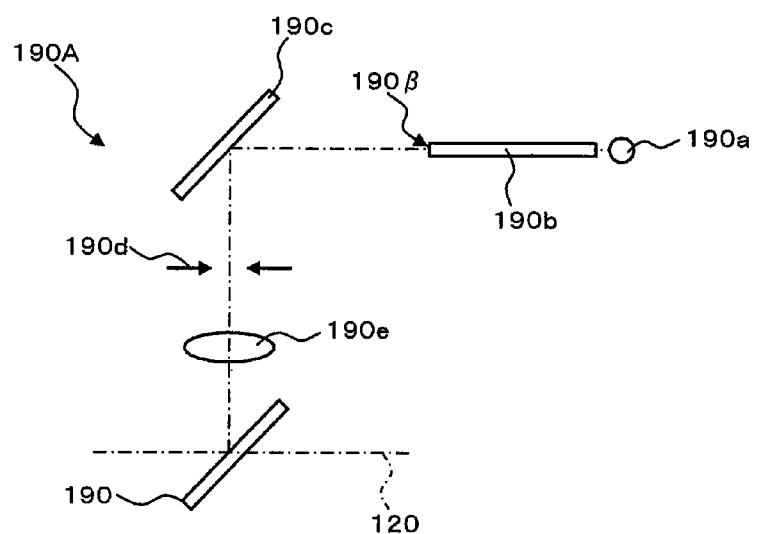
FIGS. 2A and 2B is a schematic configuration diagram showing an example of the configuration of an alignment optical system installed in a retinal camera unit in a preferred embodiment of the fundus oculi observation device according to the present invention.

The alignment optical system 190A comprises an alignment light source 190a consisting of, for example, LED for emitting light such as a near-infrared light (alignment light), a light guide 190b, a reflection mirror 190c, a two-hole aperture 190d, and a relay lens 190e as well as the half mirror 190 as shown in FIG. 2A.

Figure 2B:
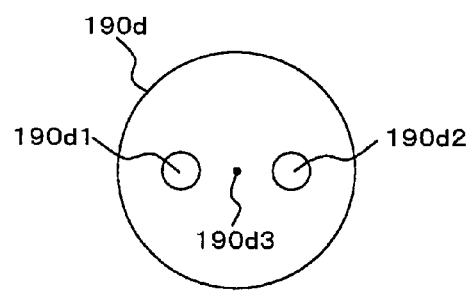

The two-hole aperture 190d has two holes 190d1 and 190d2 as shown in FIG. 2B. The holes 190d1 and 190d2 are formed at, for example, a symmetric position at the center position 190d3 of the circular two-hole aperture 190d. The two-hole aperture 190d is arranged such that the center position 190d3 is located on the optical axis of the alignment optical system 190A.

The alignment light ejected from an ejection end 190β (beta) of the light guide 190b is reflected by the reflection mirror 190c and guided to the two-hole aperture 190d. (Part of) the alignment light passing through the holes 190d1 and 190d2 of the two-hole aperture 190d are guided to the aperture mirror 112, passing through the relay lens 190e and being reflected by the half mirror 190. Then, the relay lens 190e makes the image of the ejection end 190β of the light guide 190b intermediately focus on the center position of the aperture 112a on the aperture mirror 112 (on the optical axis of the imaging optical system 120). The alignment light that has passed through the aperture 112a of the aperture mirror 112 is projected onto the cornea of the eye E via an objective lens 113.

Herein, when the positional relationship between the eye E and a retinal camera unit 1A (objective lens 113) is appropriate, that is, when the distance between the eye E and the retinal camera unit 1A (working distance) is appropriate and the optical axis of the optical system of the retinal camera unit 1A and the eye axis of the eye E (top position of the cornea) are (substantially) coincident with each other, the two light fluxes formed by the two-hole aperture 190d (alignment light fluxes) are projected onto the eye E so as to be focused on the intermediate position between the top of the cornea and the center of corneal curvature.

The corneal reflection lights of the two alignment light fluxes (alignment lights) are received by the imaging devices 10a via the imaging optical system 120. The photographed images from the imaging devices 10a are displayed on a display device such as a touch panel monitor 11 or the display of a calculation and control unit 200 (to be described later). The display feature of the alignment light at this time is shown in FIGS. 3A and 3B.

Figure 3A:
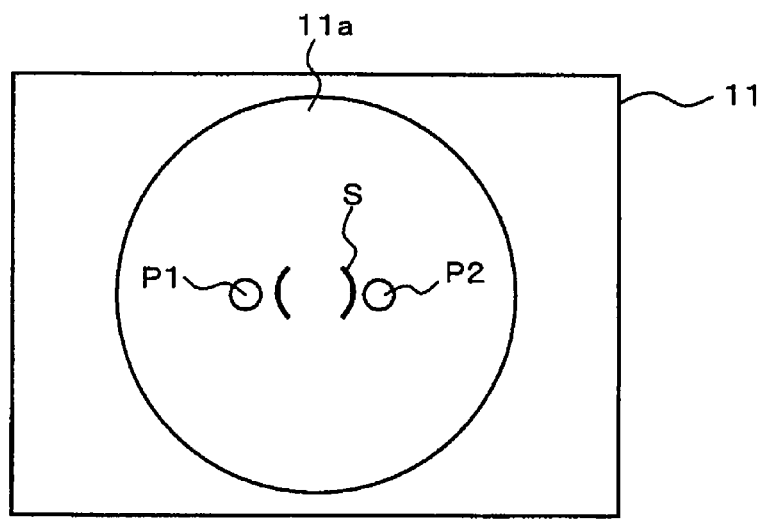
FIGS. 3A and 3B is a schematic diagram for explaining an example of an alignment operation in a preferred embodiment of the fundus oculi observation device according to the present invention.
Figure 3B:
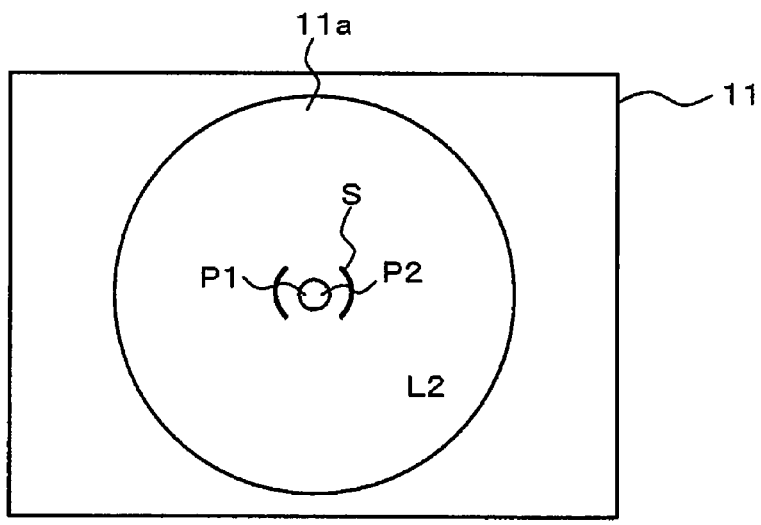

The symbol S in FIGS. 3A and 3B indicates a scale having a bracket shape, and symbols P1 and P2 indicate the light-receiving image of the two alignment light fluxes (alignment bright point). In addition, scale S is displayed on the touch panel monitor 11 such that its center position coincides with the optical axis of the imaging optical system 120.

When the positions of the eye E and the retinal camera unit 1A are misaligned in the up-and-down direction (y direction) or the right-and-left direction (x direction), the alignment bright points P1 and P2 are displayed in positions misaligned in scale S in the up-and-down direction or the right-and-left direction as shown in FIG. 3(A). In addition, when the working distance is not appropriate, the alignment bright points P1 and P2 are each displayed at separate positions.

On the other hand, when the positions in the x-y direction of the eye E and the retinal camera unit 1A are coincident with each other and the working distance is appropriate, the alignment bright points P1 and P2 are displayed in scale S overlapping with each other as shown in FIG. 3B. An examiner performs the alignment by adjusting the positional relationship between the eye E and the retinal camera unit 1A such that the alignment bright points P1 and P2 overlap each other and are displayed in scale S.

[Configuration of OCT Unit]

Next, the configuration of the OCT unit 150 will be described referring to FIG. 5. The OCT unit 150 shown in FIG. 3 is a device configured to form a tomographic image of the fundus oculi based on optically obtained data (data detected by a CCD 184 described later). The OCT unit 150 has almost the same optical system as the conventional optical image measurement device. That is, the OCT unit 150 has: an interferometer that splits the light emitted from the light source into a reference light and a signal light and generates interference light by superposing the reference light passed through a reference object and the signal light passed through a measurement object (fundus oculi Ef); and a part configured to detect this interference light and output signals as the result of the detection (detection signals) toward the arithmetic and control unit 200. The arithmetic and control unit 200 forms a tomographic image of the measurement object (fundus oculi Ef), by analyzing the detection signals.

A low coherence light source 160 is composed of a broadband light source, such as a super luminescent diode (SLD) and a light emitting diode (LED), configured to emit a low coherence light L0. This low coherence light L0 is, for example, a light that has a wavelength of the near-infrared region and has a temporal coherence length of approximately several tens of micrometers. The low coherence light L0 has a longer wavelength than the illumination light (wavelength: about 400 nm through 800 nm) of the retinal camera unit 1A, for example, a wavelength included in a range of about 800 nm through 900 nm.

The low coherence light L0 emitted from the low coherence light source 160 is guided to an optical coupler 162 through an optical fiber 161 composed of, for example, a single mode fiber or a PM (Polarization maintaining) fiber. The optical coupler 162 splits this low coherence light L0 into a reference light LR and the signal light LS.

Although the optical coupler 162 acts as both a part (splitter) for splitting light and a part (coupler) for superposing lights, it will be herein referred to as an "optical coupler" idiomatically.

The reference light LR generated by the optical coupler 162 is guided by an optical fiber 163 composed of a single mode fiber or the like, and emitted from the end face of the fiber. The emitted reference light LR is converged into a parallel light flux by a collimator lens 171, passed through a glass block 172 and a density filter 173, and then reflected by a reference mirror 174 (reference object).

The reference light LR reflected by the reference mirror 174 is converged to the fiber end face of the optical fiber 163 by the collimator lens 171 again through the density filter 173 and the glass block 172. The converged reference light LR is guided to the optical coupler 162 through the optical fiber 163.

The glass block 172 and the density filter 173 act as a delaying part for making the optical path lengths (optical distances) of the reference light LR and the signal light LS coincide, and also as a dispersion correction part for making the dispersion characteristics of the reference light LR and the signal light LS coincide.

Furthermore, the reference mirror 174 is configured so as to move in the traveling direction (the direction of the arrow pointing both sides shown in FIG. 5) of the reference light LR. As a result, the optical path length of the reference light LR according to the axial length of the eye E, etc. is ensured. The reference mirror 174 is moved by a drive mechanism (a reference mirror drive mechanism 243 described later; refer to FIG. 7) including a driving part such as a motor.

On the other hand, the signal light LS generated by the optical coupler 162 is guided to the end of the connection line 152 through an optical fiber 164 composed of a single mode fiber or the like. The conductive optical fiber 152a runs inside the connection line 152. Herein, the optical fiber 164 and the optical fiber 152a may be composed of a single optical fiber, or may be jointly formed by connecting the end faces of the respective fibers. In either case, it is sufficient as far as the optical fiber 164 and 152a are configured to be capable of transferring the signal light LS between the retinal camera unit 1A and the OCT unit 150.

The signal light LS is guided through the inside of the connection line 152 and led to the retinal camera unit 1A. Then, the signal light LS enters into the eye E through the lens 142, the scanning unit 141, the dichroic mirror 134, the imaging lens 126, the relay lens 125, the variable magnifying lens 124, the imaging diaphragm 121, the aperture 112a of the aperture mirror 112, and the objective lens 113. The barrier filter 122 and 123 are retracted from the optical path in advance, respectively, when the signal light LS is made to enter the eye E.

The signal light LS having entered the eye E forms an image on the fundus oculi (retina) Ef and is then reflected. At this moment, the signal light LS is not only reflected on the surface of the fundus oculi Ef, but also scattered at the refractive index boundary after reaching the deep area of the fundus oculi Ef. As a result, the signal light LS passed through the fundus oculi Ef is a light containing information reflecting the state of the surface of the fundus oculi Ef and information reflecting the state of backscatter at the refractive index boundary of the deep area tissue of the fundus oculi Ef. This light may be simply referred to as "fundus oculi reflection light of the signal light LS."

The fundus oculi reflection light of the signal light LS travels reversely on the above path within the retinal camera unit 11A to be converged at the end face 152b of the optical fiber 152a, enters into the OCT unit 150 through the optical fiber 152a, and returns to the optical coupler 162 through the optical fiber 164. The optical coupler 162 superimposes the signal light LS returning through the fundus oculi Ef and the reference light LR reflected by the reference mirror 174, thereby generating the interference light LC. The generated interference light LC is guided into a spectrometer 180 through an optical fiber 165 composed of a single mode fiber or the like.

The spectrometer 180 comprises a collimator lens 181, a diffraction grating 182, an image-forming lens 183, and a CCD 184. The diffraction grating 182 in the present embodiment is a transmission-type diffraction grating that transmits light; however, needless to say, a reflection-type diffraction grating that reflects light may also be used. Moreover, needless to say, it is also possible to adopt, in place of the CCD 184, other photo-detecting elements.

The interference light LC having entered the spectrometer 180 is split (resolved into spectra) by the diffraction grating 182 after converged into a parallel light flux by the collimator lens 181. The split interference light LC forms an image on the image pick-up surface of the CCD 184 by the image-forming lens 183. The CCD 184 receives the interference light LC and converts to electrical detection signals, and outputs the detection signals to the arithmetic and control unit 200.

[Configuration of Arithmetic and Control Unit]

Next, the configuration of the arithmetic and control unit 200 will be described. The arithmetic and control unit 200 performs a process of analyzing the detection signals inputted from the CCD 184 of the spectrometer 180 of the OCT unit 150, and forming tomographic images of the fundus oculi Ef of the eye E. A technique for this analysis is the same as a conventional technique for the Fourier domain OCT.

Further, the arithmetic and control unit 200 performs a process of forming (image data of) a 2-dimensional image showing the state of the surface (retina) of the fundus oculi Ef, based on the video signals outputted from the imaging devices 10 and 12 of the retinal camera unit 1A.

Furthermore, the arithmetic and control unit 200 executes control of each part of the retinal camera unit 1A and the OCT unit 150.

Control of the retinal camera unit 1A is, for example: control of emission of illumination light by the observation light source 101 or the imaging light source 103; control of insertion/retraction operations of the exciter filters 105 and 106 or the barrier filters 122 and 123 to/from the optical path; control of the operation of a display device such as the LCD 140; control of shift of the illumination diaphragm 110 (control of the diaphragm value); control of the diaphragm value of the imaging diaphragm 121; control of shift of the variable magnifying lens 124; control of switching the alignment light source 190a on/off; and control of the operation of the Galvano mirrors 141A and 141B inside the scanning unit 141.

On the other hand, control of the OCT unit 150 is, for example: control of emission of the low coherence light L0 by the low coherence light source 160; control of shift of the reference mirror 174; and control of the accumulated time of the CCD 184.

Figure 6:
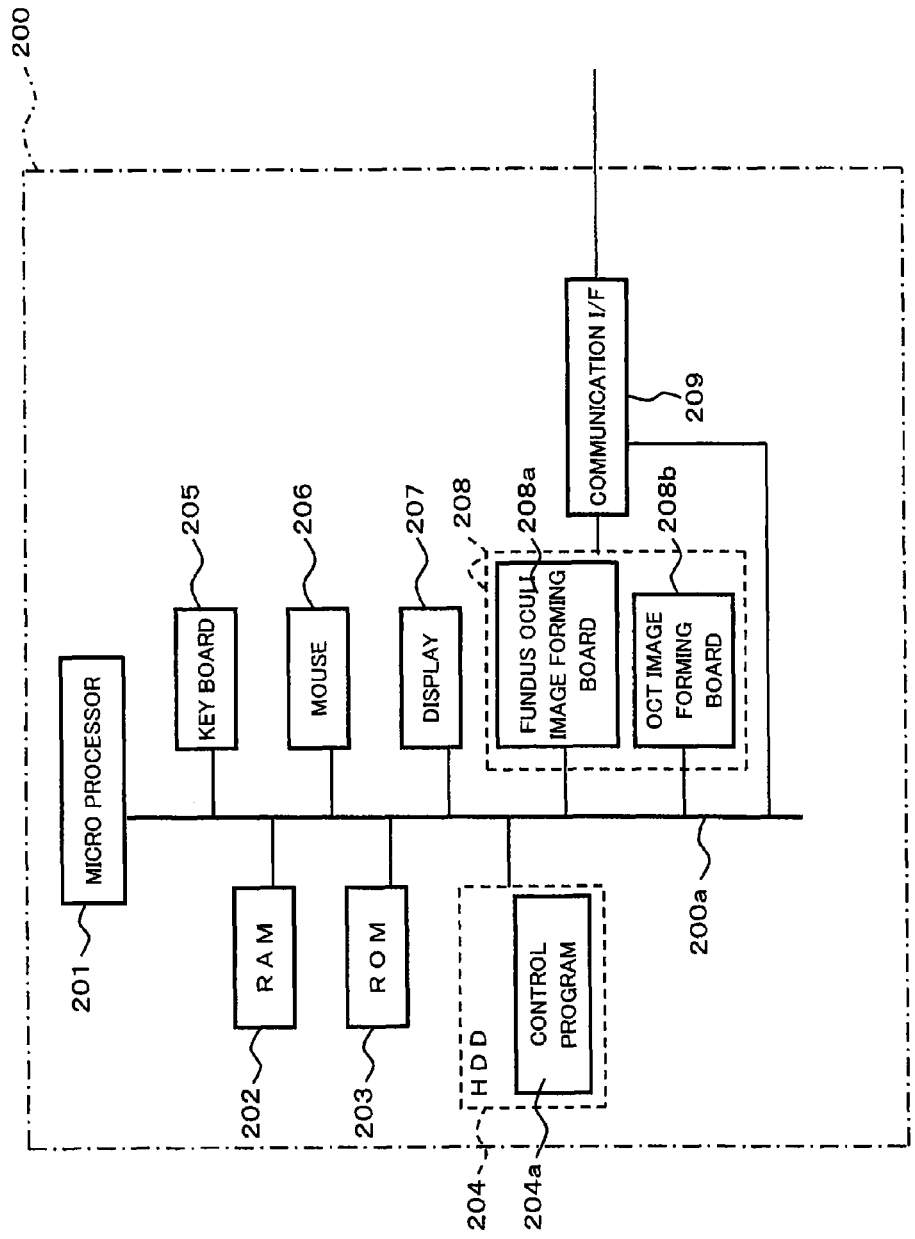
FIG. 6 is a schematic block diagram showing an example of the hardware configuration of an arithmetic and control unit in a preferred embodiment of the fundus oculi observation device according to the present invention.

An example of the hardware configuration of the arithmetic and control unit 200 that acts as described above will be described referring to FIG. 6. The arithmetic and control unit 200 is provided with the same hardware configuration as that of a conventional computer. To be specific, the arithmetic and control unit 200 comprises: a microprocessor 201 (CPU, MPU, etc.), a RAM202, a ROM203, a hard disk drive (HDD) 204, a keyboard 205, a mouse 206, a display 207, an image forming board 208, and a communication interface (I/F) 209. These parts are connected via a bus 200a.

The microprocessor 201 executes operations characteristic to the present embodiment, by loading a control program 204a stored in the hard disk drive 204, onto the RAM 202.

Further, the microprocessor 201 executes control of each part of the device described above, various arithmetic processes, etc. Moreover, the microprocessor 201 executes control of each part of the device corresponding to an operation signal from the keyboard 205 or the mouse 206, control of a display process by the display 207, and control of a transmission/reception process of various data, control signals and so on by the communication interface 209.

The keyboard 205, the mouse 206 and the display 207 are used as user interfaces in the fundus oculi observation device 1. The keyboard 205 is used as, for example, a device for typing letters, figures, etc. The mouse 206 is used as a device for performing various input operations to the display screen of the display 207.

Further, the display 207 is any display device composed of an LCD, a CRT (Cathode Ray Tube) display or the like. The display 207 displays various images of the fundus oculi Ef formed by the fundus oculi observation device 1, and displays various screens such as an operation screen and a set-up screen.

The user interface of the fundus oculi observation device 1 is not limited to the above configuration, and may be configured by using any user interface having a function of displaying and outputting various information, and a function of inputting various information, such as a track ball, a control lever, a touch panel type of LCD, and a control panel for ophthalmology examinations.

The image forming board 208 is a dedicated electronic circuit for a process of forming (image data of) images of the fundus oculi Ef of the eye E. This image forming board 208 is provided with a fundus oculi image forming board 208a and an OCT image forming board 208b.

The fundus oculi image forming board 208a is a dedicated electronic circuit that operates to form image data of fundus oculi images based on the video signals from the imaging device 10 and the imaging device 12 of the retinal camera unit 1A.

Further, the OCT image forming board 208b is a dedicated electronic circuit that operates to form image data of tomographic images of the fundus oculi Ef, based on the detection signals from the CCD 184 of the spectrometer 180 in the OCT unit 150.

By providing the image forming board 208, it is possible to increase the processing speed for forming image data of fundus oculi images and tomographic images.

The communication interface 209 performs a process of sending control signals from the microprocessor 201, to the retinal camera unit 1A or the OCT unit 150. Moreover, the communication interface 209 performs a process of receiving video signals from the imaging devices 10 and 12 of the retinal camera unit 1A and detection signals from the CCD 184 of the OCT unit 150, and inputting the signals to the image forming board 208. At this time, the communication interface 209 operates to input the video signals from the imaging devices 10 and 12, to the fundus oculi image forming board 208a, and input the detection signal from the CCD 184, to the OCT image forming board 208b.

Further, in a case where the arithmetic and control unit 200 is connected to a network such as a LAN (Local Area Network) and the Internet, it is possible to configure so as to be capable of data communication via the network, by providing the communication interface 209 with a network adapter like a LAN card or communication equipment like a modem. In this case, by mounting a server accommodating the control program 204a on the network, and at the same time, configuring the arithmetic and control unit 200 as a client terminal of the server, it is possible to cause the fundus oculi observation device 1 to execute the operation according to the present invention.

[Configuration of Control System]

Figure 7:
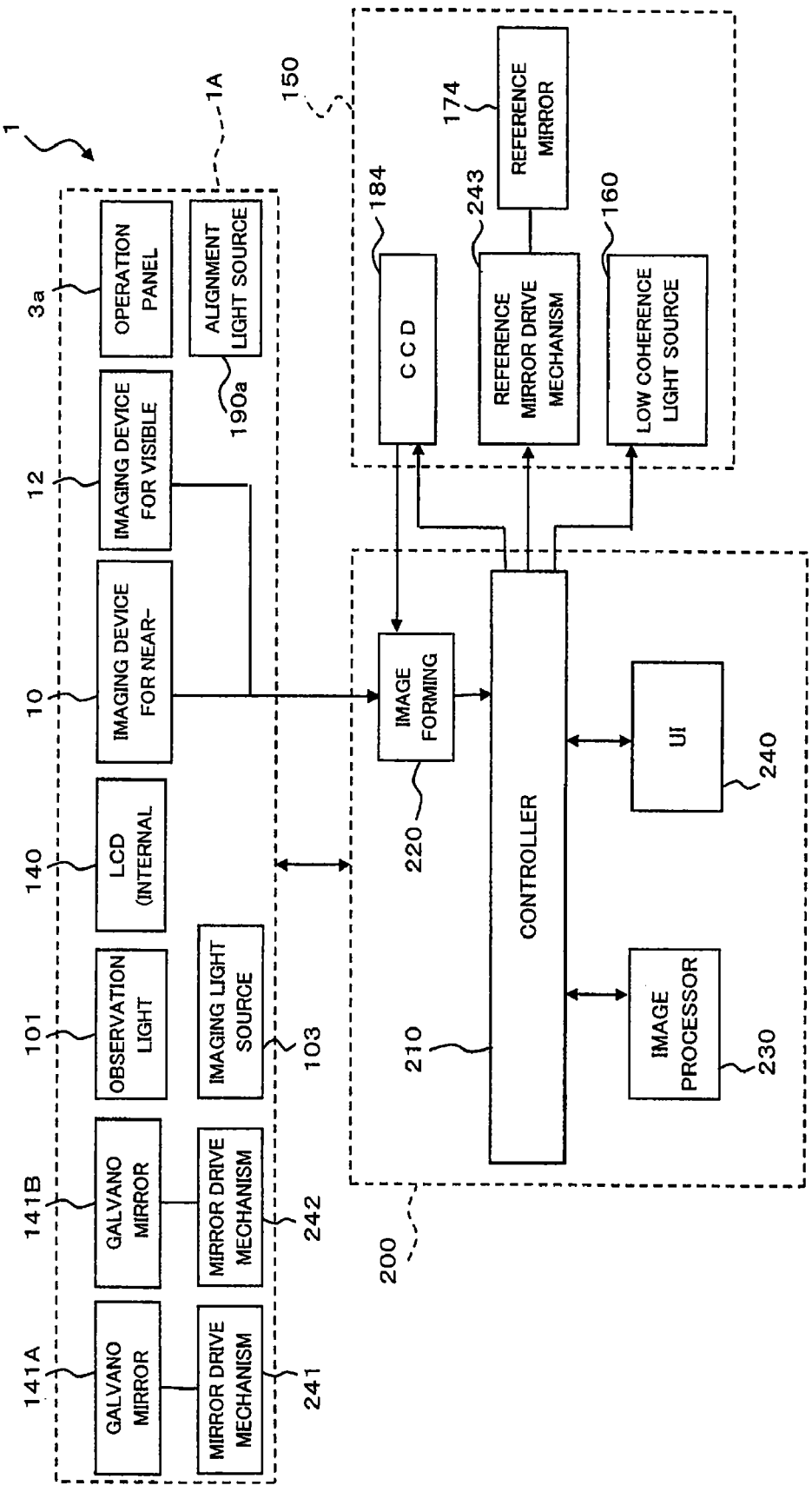
FIG. 7 is a schematic block diagram showing an example of the configuration of a control system in a preferred embodiment of the fundus oculi observation device according to the present invention.
Figure 8:
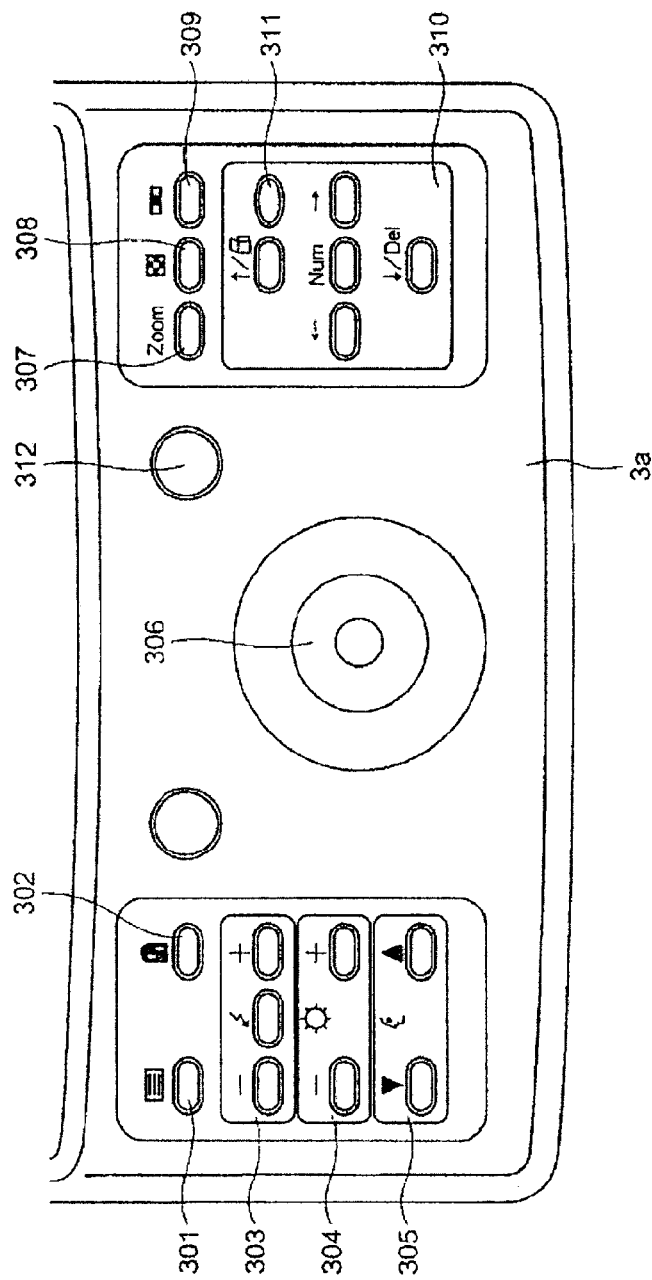
FIG. 8 is a schematic diagram showing an example of the appearance of an operation panel in a preferred embodiment of the fundus oculi observation device according to the present invention.
Figure 9:
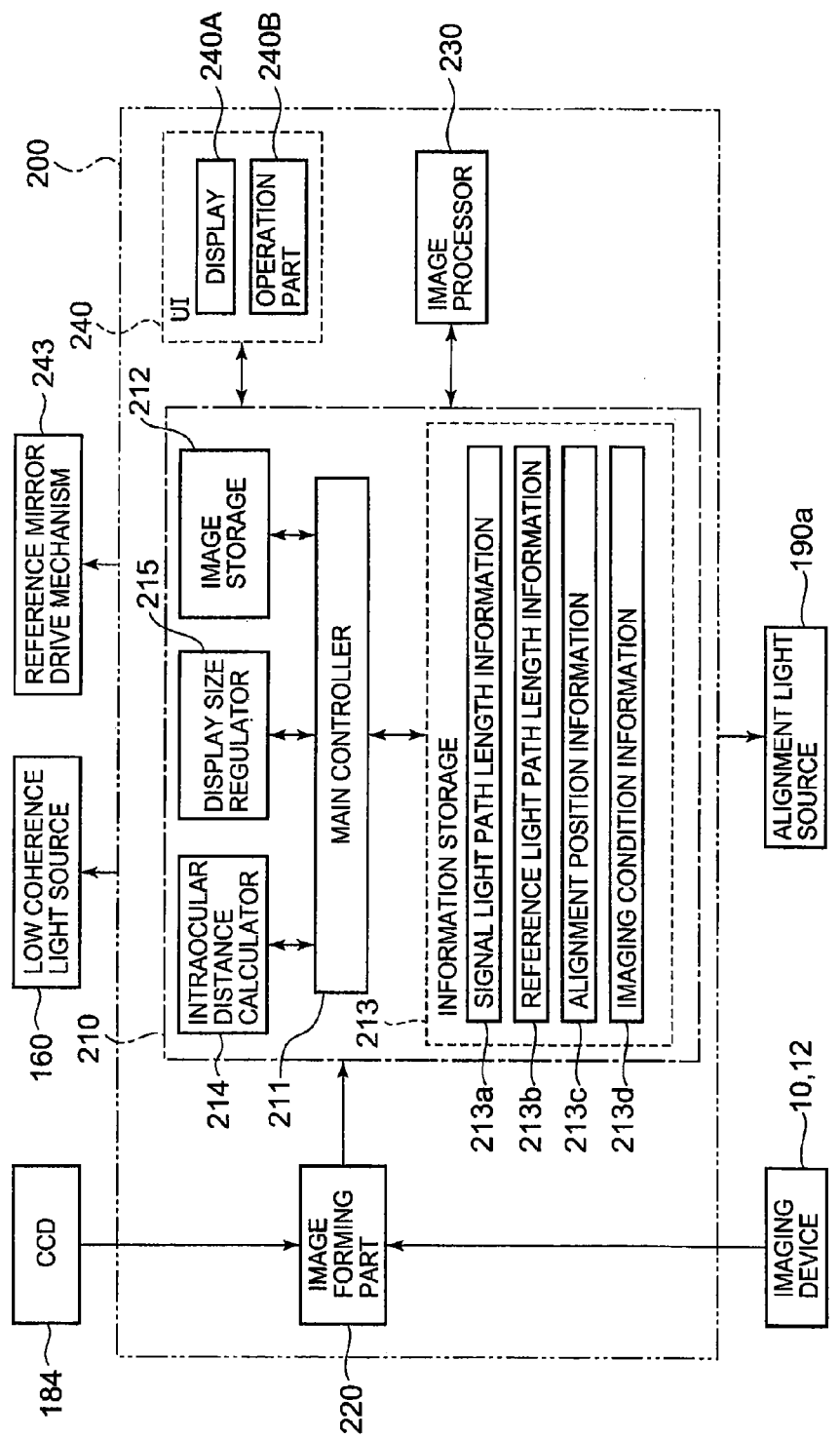
FIG. 9 is a schematic block diagram showing an example of the configuration of an arithmetic and control unit in a preferred embodiment of the fundus oculi observation device according to the present invention.

The configuration of the control system of the fundus oculi observation device 1 will be described referring to FIGS. 7 to 9. FIG. 7 is a block diagram showing a part related to the operations and processes according to the present embodiment particularly selected from among constituents composing the fundus oculi observation device 1. FIG. 8 shows one example of the configuration of the operation panel 3a disposed to the retinal camera unit 1A. FIG. 9 is a block diagram showing a detailed configuration of the arithmetic and control unit 200.

(Controller)

The control system of the fundus oculi observation device 1 is configured mainly having a controller 210 of the arithmetic and control unit 200. The controller 210 comprises the microprocessor 201, the RAM202, the ROM203, the hard disk drive 204 (control program 204a), and the communication interface 209.

The controller 210 executes the aforementioned controlling processes through the microprocessor 201 operating based on the control program 204a. Specifically, the controller executes control of the mirror drive mechanisms 241 and 242 of the retinal camera unit 1A for causing the Galvano mirrors 141A and 141B to independently operate, control of the reference mirror drive mechanism 243 for moving the reference mirror 174 in the traveling direction of a reference light LR, control of switching the alignment light source 190a on/off, and the like.

Further, the controller 210 executes control for causing the display 207 of the user interface 240 to display two kinds of images captured by the fundus oculi observation device 1: that is, a 2-dimensional image (fundus oculi image Ef') of the surface of the fundus oculi Ef obtained by the retinal camera unit 1A, and a tomographic image of the fundus oculi Ef formed based on the detection signals obtained by the OCT unit 150 (or a 3-dimensional image formed based on the tomographic images). These images may be displayed on the display 207 separately, or may be displayed side by side simultaneously. The details of the configuration of the controller 210 will be described later with reference to FIG. 9.

(Image Forming Part)

An image forming part 220 performs a process of forming image data of the fundus oculi image based on the video signals from the imaging devices 10 and 12 of the retinal camera unit 1A. Moreover, the image forming part 220 performs a process of forming image data of the tomographic images of the fundus oculi Ef based on the detection signals from the CCD 184 of the OCT unit 150. The imaging forming part 220 comprises the imaging forming board 208 and the communication interface 209. In this specification, "image" may be identified with "image data" corresponding thereto.

(Image Processor)

The image processor 230 applies various image processing to image data of images formed by the image forming part 220. For example, the image processor 230 executes a process of forming image data of a 3-dimensional image of the fundus oculi Ef based on the tomographic images corresponding to the detection signal from the OCT unit 150, and various correction processes such as brightness correction and dispersion correction of the images.

Herein, image data of a 3-dimensional image is image data made by assigning pixel values to each of a plurality of voxels arranged 3-dimensionally, and is referred to as volume data, voxel data, and the like. When displaying an image based on volume data, the image processor 230 operates to apply a rendering process (such as volume rendering and MIP (Maximum Intensity Projection)) to this volume data and form image data of a pseudo 3-dimensional image seen from a specified viewing direction. On a display device such as the display 207, the pseudo 3-dimensional image based on the image data is displayed.

(User Interface)

As shown in FIG. 9, the user interface (UI) 240 comprises a display 240A composed of a display device such as the display 207, and an operation part 240B composed of an input device or an operation device such as the keyboard 205 and the mouse 206.

(Operation Panel)

Figure 15:
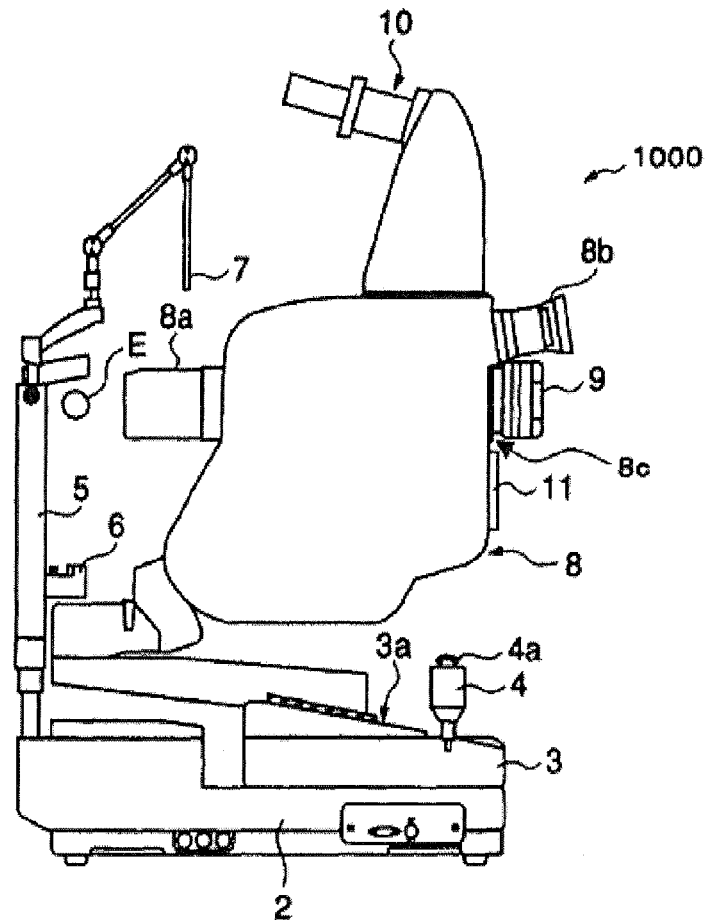
FIG. 15 is a schematic side view showing an example of the appearance of a conventional fundus oculi observation device (retinal camera).

The operation panel 3a of the retinal camera unit 1A will be described. As shown in FIG. 15, this operation panel 3a is arranged on the platform 3 of the retinal camera unit 1A, for example. The operation panel 3a according to the present embodiment is, different from the conventional configuration described in Background of the Invention, provided with an operating part used to instruct an operation for capturing an image of the surface of the fundus oculi Ef and the vicinity thereof, and an operating part used to instruct an operation for capturing a tomographic image of the fundus oculi Ef (in the conventional configuration, only the former operating part is provided). Consequently, it is possible to execute an operation for capture of an OCT image, in the same manner as when operating a conventional retinal camera.

As shown in FIG. 8, the operation panel 3a is provided with, for example, a menu switch 301, a split switch 302, an imaging light amount switch 303, an observation light amount switch 304, a jaw holder switch 305, a photographing switch 306, a zoom switch 307, an image switching switch 308, a fixation target switching switch 309, a fixation target position adjusting switch 310, a fixation target size switching switch 311, and a mode switching knob 312.

The menu switch 301 is a switch operated to display a certain menu screen for a user to select and designate various menus (such as an imaging menu for imaging a 2-dimensional image of the surface of the fundus oculi Ef, a tomographic image and the like, and a setting menu for inputting various settings). When this menu switch 301 is operated, the operation signal is inputted to the controller 210. The controller 210 causes the touch panel monitor 11 or the display 240A to display a menu screen, in response to the input of the operation signal. A controller (not shown) may be provided in the retinal camera unit 1A, whereby the controller causes the touch panel monitor 11 to display the menu screen.

The split switch 302 is a switch operated to switch on and off the split bright line for focusing (refer to Japanese Unexamined Patent Application Publication JP-A 9-066031, for example; also referred to as a split target, a split mark and so on). The configuration for projecting this split bright line onto the eye E (split bright line projection part) is housed, for example, in the retinal camera unit 1A (not shown in FIG. 1). When this split switch 302 is operated, the operation signal is inputted to the controller 210 (or the aforementioned controller inside the retinal camera unit 1A; the same hereinafter). The controller 210 projects the split bright line onto the eye E by controlling the split bright line projection part, in response to the input of this operation signal.

The imaging light amount switch 303 is a switch operated to adjust the emitted light amount of the imaging light source 103 (photographing light amount) depending on the state of the eye E (such as the degree of opacity of the lens). This imaging light amount switch 303 is provided with, for example, a photographing light amount increasing switch "+" for increasing the photographing light amount, a photographing light amount decreasing switch "−" for decreasing the photographing light amount, and a reset switch (a button in the middle) for setting the photographing light amount to a predetermined initial value (default value). When one of the imaging light amount switches 303 is operated, the operation signal is inputted to the controller 210. The controller 210 controls the imaging light source 103 in response to the inputted operation signal and adjusts the photographing light amount.

The observation light amount switch 304 is a switch operated to adjust the emitted light amount (observation light amount) of the observation light source 101. The observation light amount switch 304 is provided with, for example, an observation light amount increasing switch "+" for increasing the observation light amount, and an observation light amount decreasing switch "−" for decreasing the observation light amount. When one of the observation light amount switches 304 is operated, the operation signal is inputted to the controller 210. The controller 210 controls the observation light source 101 in response to the inputted operation signal and adjusts the observation light amount.

The jaw holder switch 305 is a switch to move the position of the jaw holder 6 shown in FIG. 15. This jaw holder switch 305 is provided with, for example, an upward movement switch (upward triangle) for moving the jaw holder 6 upward, and a downward movement switch (downward triangle) for moving the jaw holder 6 downward. When one of the jaw holder switches 305 is operated, the operation signal is inputted to the controller 210. The controller 210 controls a jaw holder movement mechanism (not shown) in response to the inputted operation signal and moves the jaw holder 6 upward or downward.

The photographing switch 306 is a switch used as a trigger switch for capturing a 2-dimensional image of the surface of the fundus oculi Ef or a tomographic image of the fundus oculi Ef. When the photographing switch 306 is operated in a state where a menu to photograph a 2-dimensional image is selected, the controller 210 that has received the operation signal controls the imaging light source 103 to emit photographing illumination light, and also causes the display 240A or the touch panel monitor 11 to display a 2-dimensional image of the surface of the fundus oculi Ef, based on the video signal outputted from the imaging device 10 having detected the fundus oculi reflection light. On the other hand, when the photographing switch 306 is operated in a state where a menu to capture a tomographic image is selected, the controller 210 that has received the operation signal controls the low coherence light source 160 to emit the low coherence light L0, and also controls the Galvano mirrors 141A and 141B to scan the signal light LS. Moreover, the controller 210 causes the display 240A or the touch panel monitor 11 to display a tomographic image of the fundus oculi Ef formed by the image forming part 220 (and image processor 230), based on the detection signal outputted from the CCD 184 that has detected the interference light LC.

The zoom switch 307 is a switch operated to change the angle of view (zoom magnification) at the time of photographing of the fundus oculi Ef. Every time this zoom switch 307 is operated, the photographing angle is set alternately to 45 degrees and 22.5 degrees, for example. When this zoom switch 307 is operated, the controller 210 that has received the operation signal controls a variable magnifying lens drive mechanism (not shown) to move the variable magnifying lens 124 in the optical axis direction of the imaging optical system 120, thereby changing the photographing angle of view.

The image switching switch 308 is a switch operated to switch displayed images. When the image switching switch 308 is operated in a state where a fundus oculi observation image (a 2-dimensional image of the surface of the fundus oculi Ef based on the video signal from the imaging device 12) is displayed on the display 240A or the touch panel monitor 11, the controller 210 having received the operation signal controls the display 240A or touch panel monitor 11 to display the tomographic image of the fundus oculi Ef. On the other hand, when the image switching switch 308 is operated in a state where a tomographic image of the fundus oculi is displayed on the display 240A or the touch pane monitor 11, the controller 210 having received the operation signal controls the display 240A or the touch panel monitor 11 to display the fundus oculi observation image.

The fixation target switching switch 309 is a switch operated to switch the position of the internal fixation target displayed by the LCD 140 (i.e. the projection position of the internal fixation target on the fundus oculi Ef). By operating this fixation target switching switch 309, "fixation position to capture the image of the peripheral region of the center of the fundus oculi (fixation position for fundus oculi center imaging)," "fixation position to capture the image of the peripheral region of macula lutea (fixation position for macula lutea imaging)" and "fixation position to capture the image of the peripheral region of papilla (fixation position for papilla imaging)" are switched in a circulative fashion, for example. In response to the operation signals from the fixation target switching switch 309, the controller 210 causes the LCD 140 to display the internal fixation target in different positions on the display surface thereof. The display positions of the internal fixation target corresponding to the above three fixation positions, for example, can be preset based on clinical data, or can be set for each eye E (or for each image of the fundus oculi Ef) in advance.

The fixation target position adjusting switch 310 is a switch operated to adjust the display position of the internal fixation target. This fixation target position adjusting switch 310 is provided with, for example, an upward movement switch for moving the display position of the internal fixation target upward, a downward movement switch for moving it downward, a leftward movement switch for moving it leftward, a rightward movement switch for moving it rightward, and a reset switch for moving it to a predetermined initial position (default position). Upon reception of the operation signal from either of these switches of the fixation target position adjusting switch 310, the controller 210 controls the LCD 140 to move the display position of the internal fixation target, in response to the operation signal.

The fixation target size switching switch 311 is a switch operated to change the size of the internal fixation target. When this fixation target size switching switch 311 is operated, the controller 210 that has received the operation signal controls the LCD 140 to change the display size of the internal fixation target. The display size of the internal fixation target can be switched, for example, between "normal size" and "enlarged size," alternately. As a result, the size of the projection image of the fixation target projected onto the fundus oculi Ef is changed. Upon reception of the operation signal from the fixation target position adjusting switch 311, the controller 210 controls the LCD 140 to change the display size of the internal fixation target, in response to the operation signal.

The mode switching knob 312 is a knob rotationally operated to select various photographing modes, such as a fundus oculi photographing mode to photograph a 2-dimensional image of the fundus oculi Ef, a B-scan mode to perform B-scan of the signal light LS, and a 3-dimensional scan mode to scan with the signal light LS 3-dimensionally. In addition, the mode switching knob 312 may be configured so as to be capable of selecting a replay mode to replay and display a captured 2-dimensional image or tomographic image of the fundus oculi Ef. In addition, it may be configured so as to be capable of selecting a photographing mode to control so that the photographing of the fundus oculi Ef would be performed immediately after scanning of the signal light LS. Control of each part of the device for causing the fundus oculi observation device 1 to execute the operation corresponding to the each mode is executed by the controller 210.

Herein, the feature of control of scanning of the signal light LS by the controller 210, and the feature of processing to the detection signal from the OCT unit 150 by the image forming part 220 and the image processor 230 will be respectively described. An explanation regarding the process by the image forming part 220, etc., to the video signal from the retinal camera unit 1A will be omitted because it is the same as the conventional process.

[Signal Light Scanning]

Scan of the signal light LS is performed by changing the directions of the reflecting surfaces of the Galvano mirrors 141A and 141B of the scanning unit 141 in the retinal camera unit 1A. By controlling the mirror drive mechanisms 241 and 242 respectively to change the directions of the reflecting surfaces of the Galvano mirrors 141A and 141B respectively, the controller 210 scans the application position of the signal light LS on the fundus oculi Ef.

When the facing direction of the reflecting surface of the Galvano mirror 141A is changed, the signal light LS is scanned in the horizontal direction (x-direction in FIG. 1) on the fundus oculi Ef. On the other hand, when the facing direction of the reflecting surface of the Galvano mirror 141B is changed, the signal light LS is scanned in the vertical direction (y-direction in FIG. 1) on the fundus oculi Ef. Further, by changing the facing directions of the reflecting surfaces of both the Galvano mirrors 141A and 141B simultaneously, it is possible to scan the signal light LS in the composed direction of the x-direction and y-direction. That is, by controlling these two Galvano mirrors 141A and 141B, it is possible to scan the signal light LS in any direction on the x-y plane.

Figure 10A:
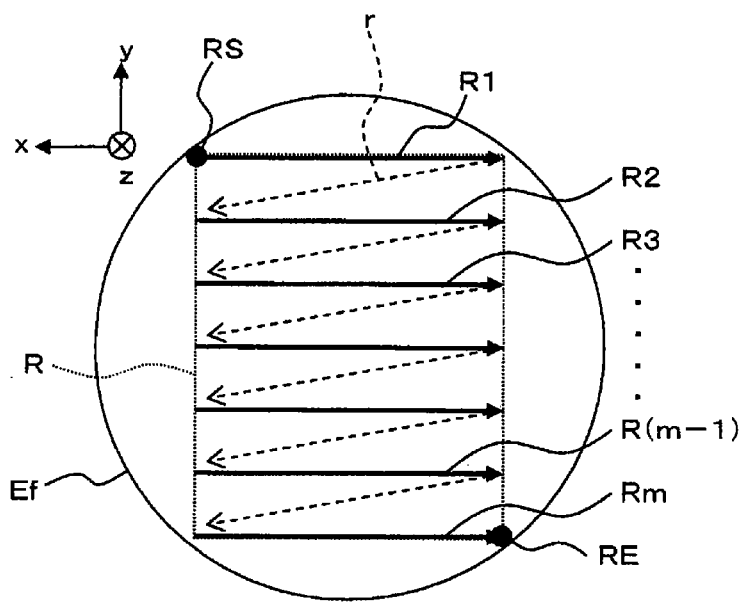
FIGS. 10A and 10B are schematic diagrams showing an example of a feature of scan of signal light in a preferred embodiment of the fundus oculi observation device according to the present invention.
Figure 10B:
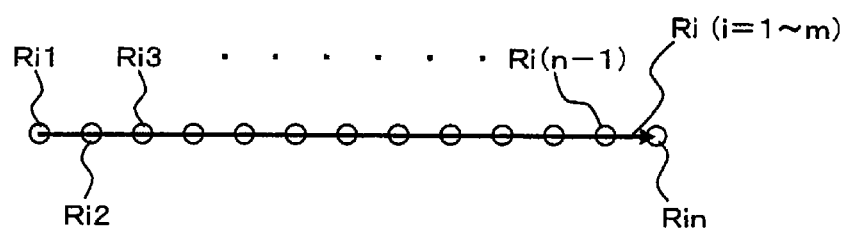

FIGS. 10A and 10B show an example of a mode of scan of the signal light LS for forming an image of the fundus oculi Ef. FIG. 10A shows an example of a mode of scan of the signal light LS, when the fundus oculi Ef is seen from a direction that the signal light LS enters the eye E (that is, seen from −z side toward +z side in FIG. 1). Further, FIG. 10B shows one example of the feature of arrangement of scanning points (positions at which image measurement is carried out) on each scanning line on the fundus oculi Ef.

As shown in FIG. 10A, the signal light LS is scanned within a rectangular-shaped scanning region R that has been preset. Within this scanning region R, a plurality of (m number of) scanning lines R1 through Rm are set in the x-direction. When the signal light LS is scanned along the respective scanning lines Ri (i=1 through m), detection signals of the interference light LC are generated.

Herein, a direction of each scanning line Ri will be referred to as the "main scanning direction" and a direction orthogonal thereto will be referred to as the "sub-scanning direction". Accordingly, scanning of the signal light LS in the main scanning direction is performed by changing the facing direction of the reflecting surface of the Galvano mirror 141A, and scanning in the sub-scanning direction is performed by changing the facing direction of the reflecting surface of the Galvano mirror 141B.

On each scanning line Ri, as shown in FIG. 10B, a plurality of (n number of) scanning points Ri1 through Rin are preset.

In order to execute the scanning shown in FIGS. 10A and 10B, the controller 210 firstly controls the Galvano mirrors 141A and 141B to set the target of the signal light LS entering into the fundus oculi Ef to a scan start position RS (scanning point R11) on the first scanning line R1. Subsequently, the controller 210 controls the low coherence light source 160 to flush the low coherence light L0, thereby making the signal light LS enter the scan start position RS. The CCD 184 receives the interference light LC based on the fundus oculi reflection light of this signal light LS at the scan start position RS, and outputs the detection signal to the controller 210.

Next, the controller 210 controls the Galvano mirror 141A to scan the signal light LS in the main scanning direction and set the incident target of the signal light LS to a scanning point R12, and makes the low coherence light L0 flushed to make the signal light LS enter into the scanning point R12. The CCD 184 receives the interference light LC based on the fundus oculi reflection light of this signal light LS at the scanning point R12, and then outputs the detection signal to the controller 210.

Likewise, the controller 210 obtains detection signals outputted from the CCD 184 in response to the interference light LC for each scanning point, by flushing the low coherence light L0 at each scanning point while shifting the incident target of the signal light LS from scanning point R13 to R14, - - - , R1 (n−1), and R1n in order.

When the measurement at the last scanning point R1n of the first scanning line R1 is finished, the controller 210 controls the Galvano mirrors 141A and 141B simultaneously to shift the incident target of the signal light LS to the first scanning point R21 of the second scanning line R2 following a line switching scan r. Then, by conducting the previously described measurement on each scanning point R2j (j=1 through n) of this second scanning line R2, detection signals corresponding to the respective scanning points R2j are obtained.

Likewise, the measurement is conducted for each of the third scanning line R3, - - - , the m−1th scanning line R(m−1), the mth scanning line Rm to obtain the detection signals corresponding to the respective scanning points. Symbol RE on a scanning line Rm is a scan end position corresponding to a scanning point Rmn.

As a result, the controller 210 obtains m×n number of detection signals corresponding to m×n number of scanning points Rij (i=1 through m, j=1 through n) within the scanning region R. Hereinafter, a detection signal corresponding to the scanning point Rij may be represented by Dij.

Such interlocking control of the shift of scanning points and the emission of the low coherence light L0 can be realized by synchronizing, for instance, timing for transmission of control signals to the mirror drive mechanisms 241 and 242 and timing for transmission of control signals (output request signals) to the low coherence light source 160.

As described above, when each of the Galvano mirrors 141A and 141B is operated, the controller 210 stores the position of each scanning line Ri and the position of each scanning point Rij (coordinates on the x-y coordinate system) as information representing the content of the operation. This stored content (scan position information) is used in an image forming process as in conventional one.

[Image Processing]

Next, an example of a process on OCT images (tomography images of the fundus oculi Ef) by the image forming part 220 and the image processor 230 will be described.

The image forming part 220 executes the formation process of tomographic images of the fundus oculi Ef along each scanning line Ri (main scanning direction). Further, the image processor 230 executes the formation process of a 3-dimensional image of the fundus oculi Ef based on these tomographic images formed by the image forming part 220, etc.

The formation process of a tomographic image by the image forming part 220, as in the conventionally one, includes a 2-step arithmetic process. In the first step of the arithmetic process, based on a detection signal Dij corresponding to each scanning point Rij, an image in the depth-wise direction (z-direction in FIG. 1) of the fundus oculi Ef at the scanning point Rij is formed.

Figure 11:
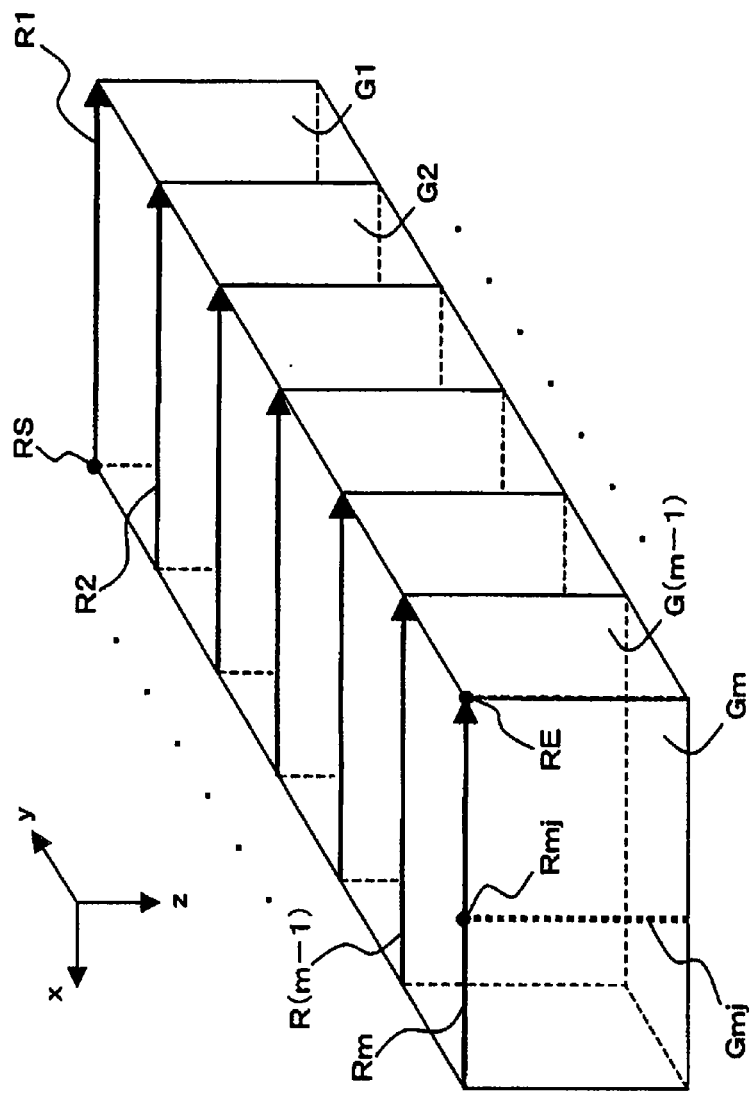
FIG. 11 is a schematic diagram showing an example of a feature of scan of signal light and a feature of a tomographic image formed along each scanning line in the preferred embodiment of the fundus oculi observation device according to the present invention.

FIG. 11 shows a mode of a tomographic image formed by the image forming part 220. In the second step of the arithmetic process, on each scanning line Ri, based on the images in the depth-wise direction at the n number of scanning points Ri1 through Rin, a tomographic image Gi of the fundus oculi Ef along the scanning line Ri is formed. Then, the image forming part 220 determines the arrangement and the distance of the scanning points Ri1 through Rin referring to the positional information (scan position information described before) of the scanning points Ri1 through Rin, and forms a tomographic image Gi along this scanning line Ri. Through the above process, m number of tomographic images (a group of tomographic images) G1 through Gm at different positions in the sub-scanning direction (y-direction) are obtained.

Here, the formation process of a 3-dimensional image of the fundus oculi Ef by the image processor 230 will be explained. A 3-dimensional image of the fundus oculi Ef is formed based on the m number of tomographic images obtained through the above arithmetic process. The image processor 230 forms a 3-dimensional image of the fundus oculi Ef by performing a known interpolating process to interpolate an image between the adjacent tomographic images Gi and G (i+1).

Here, the image processor 230 determines the arrangement and the distance of each scanning line Ri while referring to the positional information of each scanning line Ri to form this 3-dimensional image. For this 3-dimensional image, a 3-dimensional coordinate system (x,y,z) is set, based on the positional information (the scan position information) of each scanning point Rij and the z-coordinate in the depth-wise image.

Furthermore, based on this 3-dimensional image, the image processor 230 can form a tomographic image of the fundus oculi Ef at a cross-section in any direction other than the main scanning direction (x-direction). Once the cross-section is designated, the image processor 230 determines the position of each scanning point (and/or an interpolated depth-wise image) on this designated cross-section, and extracts a depth-wise image at each determined position (and/or an interpolated depth-wise image), thereby forming a tomographic image of the fundus oculi Ef at the designated cross-section by arranging plural extracted depth-wise images.

Furthermore, an image Gmj shown in FIG. 11 represents an image in the depth-wise direction (z-direction) at the scanning point Rmj on the scanning line Rm. A depth-wise image at each scanning point Rij on the scanning line Ri formed by the first-step arithmetic process is represented as "image Gij."

[Detailed Configuration of Arithmetic and Control Device]

The details of the configuration of the controller 210 of the arithmetic and control device 200 will be described referring to FIG. 9. The controller 210 includes a main controller 211, an image storage 212, an information storage 213, an intraocular distance calculator 214, and a display size regulator 215.

(Main Controller)

The main controller 211 includes a microprocessor 201 or the like, and controls each part of the fundus oculi observation device 1 described above).

(Image Storage)

The image storage 212 stores image data of a 2-dimensional image (fundus oculi image Ef') of the surface of the fundus oculi Ef, and image data of a tomographic image formed by the image forming part 220. The image storage 212 may be configured to store data to become the basis of image data of a tomographic image. This data is obtained by Fourier transform of a detection signal (spectral data of the interference light LC) inputted from the CCD 184, and shows the signal intensity corresponding to the depth of the fundus oculi Ef. By imaging the data of the signal intensity for each depth (signal intensity data), image data of a tomographic image is formed.

A process of storing the image data into the image storage 212 and a process of reading out the image data from the image storage 212 are executed by the main controller 211. The main controller 211 causes the image storage 212 to store the image data formed by the image forming part 220 etc. by linking to identification information (patient ID, patient name, etc.) of a subject inputted in advance. The image storage 212 includes a storage device such as a hard disk drive 204.

(Information Storage)

The information storage 213 stores various kinds of information supplied for an arithmetic process or control process executed by the arithmetic and control device 200, and includes a storage device such as a hard disk drive. Into the information storage 213 of the present embodiment, signal light path length information 213a, reference light path length information 213b, alignment position information 213c and imaging condition information 213d are stored.

The signal light path length information 213a is information showing the length of an optical path of the signal light LS (a signal light path). That is, the signal light path length information 213a shows the optical path length of the light traveling from the optical coupler 162 of the OCT unit 150 to the objective lens 113 through the optical fiber 164, the optical fiber 152a within the connection line 152, the lens 142, the scanning unit 141, the dichroic mirror 134, the imaging lens 126, the relay lens 125, the half mirror 190, the variable magnifying lens 124, the imaging diaphragm 121, and the aperture 112a of the aperture mirror 112. The optical path length of the signal light LS is determined in accordance with the design of the optical system of the fundus oculi observation device 1. The signal light path length information 213a is previously stored in the information storage 213.

The reference light path length information 213b is information showing the length of an optical path of the reference light LR (reference light path). The reference mirror 174 is controlled by the main controller 211 so as to move. More specifically, the main controller 211 sends driving pulses of a number depending on a targeted movement distance, to the reference mirror drive mechanism 243. The reference mirror drive mechanism 243 moves the reference mirror 174 based on the driving pulses.

The reference mirror 174 shall be moved to a specific default position when the power is supplied. Further, the amount of movement of the reference mirror 174 by a single driving pulse is constant. Further, the information storage 213 shall previously store information on the optical path length (default optical path length information; not illustrated) of the reference light LR traveling from the optical coupler 162 to the reference mirror 174 at a default position through the optical fiber 163, the collimator lens 171, the glass block 172 and the density filter 173.

The main controller 211 calculates the displacement of the reference mirror 174 from the aforementioned default position, based on the number of the driving pulses transmitted to the reference mirror drive mechanism 243, and also calculates the optical path length of the reference light LR after the reference mirror 174 is moved, based on the calculated displacement value and the default optical path length information. The result of this calculation is stored into the information storage 213 as the reference light path length information 213b. The reference light path length information 213b is generated every time the position of the reference mirror 174 is moved.

It is also possible to install a position sensor detecting the position of the reference mirror 174 in the OCT unit 150 to configure so as to generate the reference light path length information 213b, based on the detected position of the reference mirror 174.

The alignment position information 213c is information showing the result of alignment of the optical systems 100 and 120 in the retinal camera unit 1A with the eye E. When the optical systems 100 and 120 are aligned in appropriate positions with respect to the eye E, the distance (working distance) between the cornea (vertex) of the eye E and the objective lens 113 is stored in the information storage 213 as the alignment position information 213c.

The working distance between the cornea of the eye E and the objective lens 113 may always be constant, or may be acquired every time alignment is performed. In the former case, the alignment position information 213c is always constant, and is previously stored in the information storage 213. On the other hand, in the latter case, the working distance is, for example, calculated by the controller 210, based on the amount of movement of the platform 3 slid on the base 2 in alignment.

The imaging condition information 213d is information of the measurement conditions (imaging conditions) at the time of optical measurement (imaging) for forming the fundus oculi image Ef or tomographic image Gi of the eye E. The imaging condition information 213d includes characteristic information showing the characteristics of the eye E. The characteristic information includes, for example, the results of various kinds of ophthalmic examinations. In particular, the characteristic information includes information of a characteristic of the eye E (e.g., the axial length, refractive index, etc.) affecting light for measurement such as an imaging illumination light and the signal light LS.

The characteristic information of the eye E is acquired in advance by the fundus oculi observation device 1 or other ophthalmic devices. For example, for the axial length, it is possible to use the result of calculation by the intraocular distance calculator 214, as described later. Further, it is also possible to use a general value (average value, etc.) derived from clinical data, as the characteristic information.

Further, the imaging condition information 213d may include information (optical system information) showing the state of the optical systems within the retinal camera unit 1A or OCT unit 150 at the time of optical measurement. The optical system information is, for example, an imaging magnification ratio. The imaging magnification ratio can be changed by moving the variable magnifying lens 124 in the optical axis direction.

The imaging condition information 213d is stored, linked to the identification information of the eye E. As the identification information, it is possible to use, for example, information showing the patient ID or patient name of a subject, or left/right distinction of the eye E (left eye or right eye).

(Intraocular Distance Calculator)

The intraocular distance calculator 214 calculates the distance (intraocular distance) between a position where the signal light LS enters the eye E and a position where the signal light LS is reflected by the fundus oculi Ef, based on the signal light path length information 213a, the reference light path length information 213b, the alignment position information 213c, and a detection signal inputted by the CCD 184 in response to detection of the interference light LC (or signal intensity data based on the detection signal). The intraocular distance calculator 214 corresponds to an example of the "intraocular distance calculator" in the present invention.

The process by the intraocular distance calculator 214 will be described more specifically. The signal light LS and the reference light LR are generated based on the low coherence light L0. Therefore, a component whose signal intensity becomes the maximum among components contained in the interference light LC is a component based on the signal light LS reflected at a position (depth) of the fundus oculi Ef corresponding to the position of the reference mirror 174.

In this embodiment, the position of the reference mirror 174 is set so that a specific position on the surface of the fundus oculi Ef becomes the position of the fundus oculi Ef corresponding to the position of the reference mirror 174. Consequently, among components of the signal intensity data (components corresponding to the depth of the fundus oculi Ef), a component based on the signal light LS reflected on the surface of the fundus oculi Ef has the maximum intensity.

Figure 5:
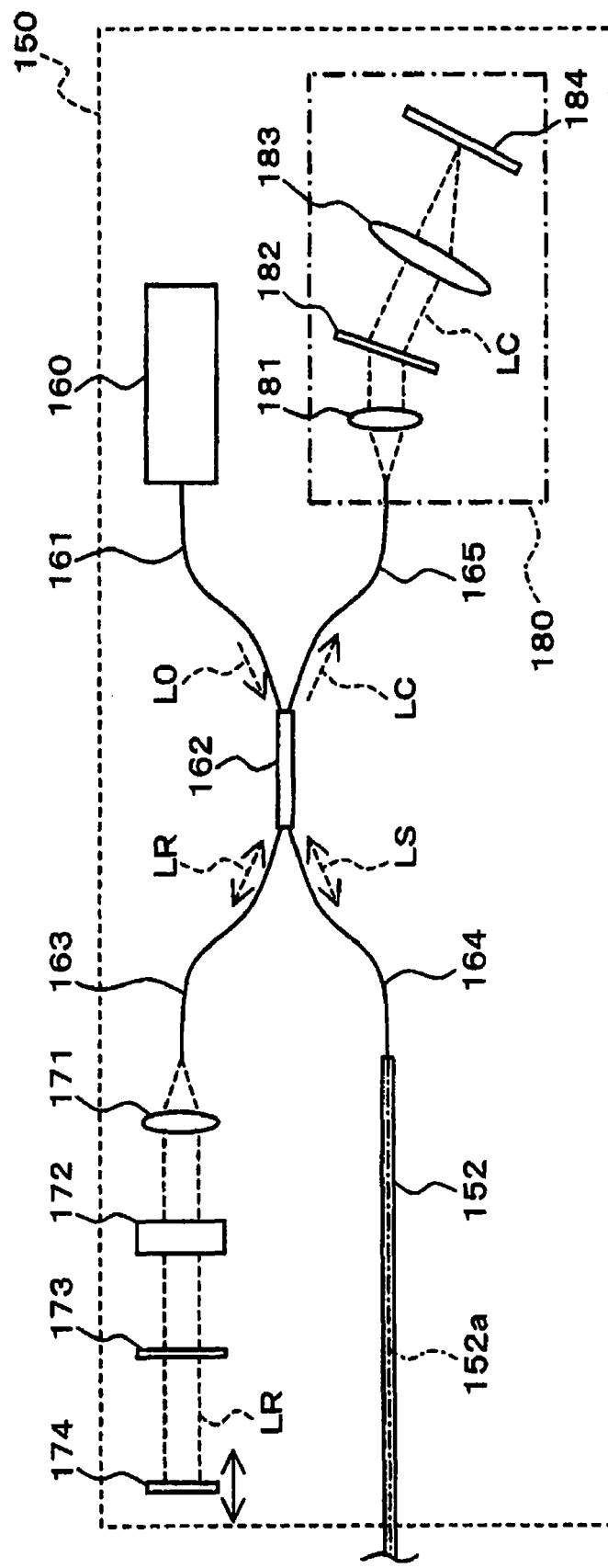
FIG. 5 is a schematic configuration diagram showing an example of the configuration of an OCT unit in a preferred embodiment of the fundus oculi observation device according to the present invention.

As apparent from the above consideration and FIGS. 1 and 5, among an optical path length $1s$ of a signal light path, an optical path length $1r$ of a reference light path, a working distance w, an intraocular distance d from a position where the signal light LS enters the eye E to a reflection position of the signal light LS in the fundus oculi Ef (a position corresponding to the position of the reference mirror 174), there is a relation of: $1r=1s+w+d$. Therefore, the intraocular distance d can be obtained from the equation $d=1r-1s-w$.

For the reflection position of the signal light LS based on the detection signal (or signal intensity data), the intraocular distance calculator 214 calculates the intraocular distance d corresponding to the reflected position by substituting the optical path length $1s$ shown in the signal light path length information 213a, the optical path length $1r$ shown in the reference light path length information 213b and the working distance w shown in the alignment position information 213c, to the equation described above.

In alignment of the optical systems 100 and 120 of the retinal camera unit 1A with the eye E, in a case where the optical axes of the optical systems 100 and 120 (substantially) coincide with a corneal vertex and the reflection position of the signal light LS corresponding to the position of the reference mirror 174 (substantially) coincides with the surface of the fundus oculi Ef, the intraocular distance d calculated by the intraocular distance calculator 214 becomes (almost) equal to the axial length of the eye E.

(Display Size Regulator)

The display size regulator 215 executes a process of regulating the display size of the fundus oculi image Ef of the fundus oculi Ef and the display size of the measurement range image showing the range of the measurement region (scanning region R) for acquiring a tomographic image Gi. In general, the scanning region R is a region of the fundus oculi Ef corresponding to a partial region of the fundus oculi image Ef'. The measurement range image is an image showing the position of the measurement region on the fundus oculi image Ef', and is, for example, an image like a frame surrounding the measurement region. The measurement range image is an image of a preset form. A specific display mode of the measurement range image will be described later.

A specific example of a process executed by the display size regulator 215 will be described. The display size regulator 215 regulates the display sizes of the fundus oculi image Ef and measurement range image, based on the imaging condition information 213d stored in the information storage 213. This process can be executed by, for example, applying an ocular optical correction method known publicly.

In addition to the axial length, it is also possible to configure to regulate the display sizes in consideration of other conditions affecting the display sizes. Such a condition is, for example, the refractive power of an anterior eye part (refractive power of the cornea or lens). Moreover, for the eye E with an intraocular lens placed, it is possible to configure to regulate the display sizes in consideration of information such as the power or color of the intraocular lens. The information may be measured by using other ophthalmic devices, or a function for measuring these types of information may also be installed in the fundus oculi observation device 1. By adding these conditions, it is possible to increase the accuracy in regulation of the display sizes.

[Usage Pattern]

Figure 12:
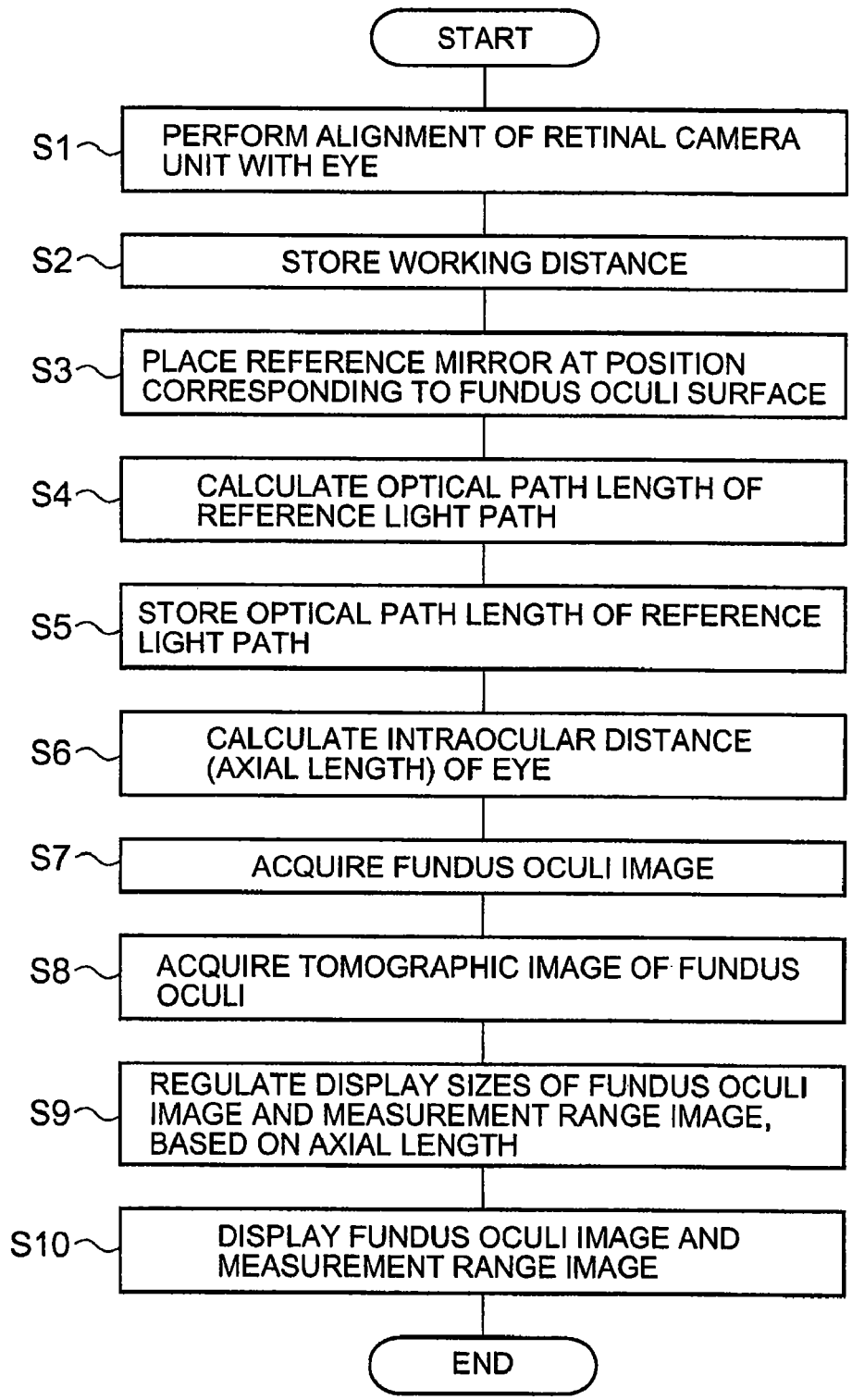
FIG. 12 is a flowchart showing one example of a usage pattern in the preferred embodiment of the fundus oculi observation device according to the present invention.

A usage pattern of the fundus oculi observation device 1 having the configuration as described above will be explained. A flowchart of FIG. 12 shows an example of the usage pattern of the fundus oculi observation device 1. The usage pattern shown in FIG. 12 is to measure the axial length of the eye E and use the result of the measurement, thereby regulating the display sizes of the fundus oculi image Ef and the measurement range image.

First, alignment of the optical systems 100 and 120 of the retinal camera unit 1A with the eye E is performed (S1). This alignment is performed by switching on the alignment light source 190a so that an alignment illumination point is projected to the eye E (described above). The main controller 211 causes the information storage 213 to store the working distance w determined by this alignment, as the alignment position information 213c (S2).

Next, the reference mirror 174 is placed at a position corresponding to the surface of the fundus oculi Ef (S3). For this purpose, for example, the position of the reference mirror 174 is regulated so that the intensity (luminance) of an image region equivalent to the surface of the fundus oculi Ef is maximized, by driving the OCT unit 150 and actually causing the display 240A to display a tomographic image of the fundus oculi Ef. Further, it is also possible to configure to drive the OCT unit 150 and acquire signal intensity data, and regulate the position of the reference mirror 174 by so that the depth component of the maximum intensity of the signal intensity data coincides with the position of the surface of the fundus oculi Ef.

The main controller 211 calculates the optical path length $1r$ of a reference light path that corresponds to the regulated position of the reference mirror 174 (S4) and causes the information storage 213 to store the calculation results as reference light path length information 213b (S5).

Subsequently, the intraocular distance calculator 214 calculates the intraocular distance d corresponding to the position of the reference mirror 174 placed in Step S3, by substituting the optical path length $1s$ of the signal light path indicated in the signal light path length information 213a, the optical path length $1r$ of the reference light path indicated in the reference light path length information 213b, and the working distance w indicated in the alignment position information 213c in the previously described equation (S6).

The calculated intraocular distance d is stored in the information storage 213 by the main controller 211 as the axial length (characteristic information, imaging condition information 213d) of the eye E. Here, it is also possible to cause the display 240A to display the value of the axial length d.

This is the end of measurement of the axial length of the eye, and the process shifts to a display process of the fundus oculi image Ef and the measurement range image.

The fundus oculi observation device 1 captures the fundus oculi image Ef of the eye E in response to, for example, an instruction from an examiner (S7). Further, the fundus oculi observation device 1 acquires the tomographic image Gi having a cross-sectional position in a measurement region of the fundus oculi Ef corresponding to a partial region of the fundus oculi image Ef (S8). Here, the tomographic image Gi may be acquired before acquisition of the fundus oculi image Ef'. Then, the main controller 211 causes the image storage 212 to store image data of the acquired fundus oculi image Ef and tomographic image Gi.

The main controller 211 reads out the image data of the fundus oculi image Ef' from the image storage 212, and also reads out the imaging condition information 213d from the information storage 213. Then, the main controller 211 sends the image data of the fundus oculi image Ef' and the imaging condition information 213d having been read out, to the display size regulator 215.

The display size regulator 215 matches the display size of the fundus oculi image Ef' with the display size of the measurement range image, based on the imaging condition information 213d (particularly the axial length) (S9).

Here, as described above, the measurement range image is an image with a preset form (e.g., the shape of a rectangular frame), and the display size regulator 215 respectively regulates the length of the x-direction and the length of the y-direction of the measurement range image with the rectangular frame shape according to the imaging condition information 213d. The display sizes may be regulated by regulating the display size of the fundus oculi image Ef', or the display size may also be regulated adapted by adjusting the display size of both images.

The main controller 211 causes the display 240A to display the fundus oculi image Ef and the measurement range image whose display sizes have been regulated by the display size regulator 125 (S10). At this moment, the tomographic image Gi of the fundus oculi Ef acquired in Step 8 may also be displayed along with the fundus oculi image Ef' and the measurement range image.

[Display Mode]

Figure 13:
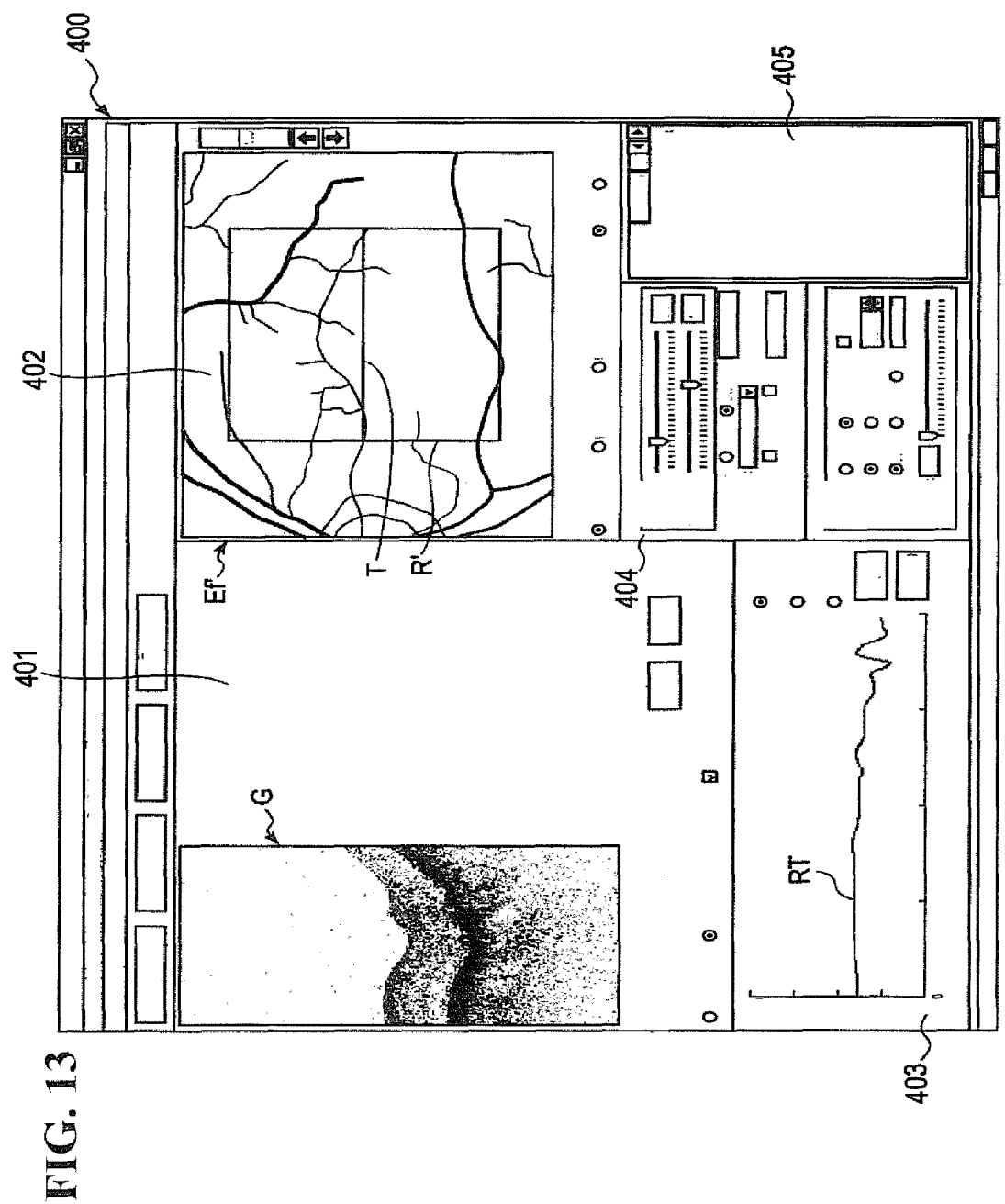
FIG. 13 is a schematic diagram showing an example of a display feature of a fundus oculi image and a measurement range in the preferred embodiment of the fundus oculi observation device according to the present invention.

An example of the display mode of the fundus oculi image Ef' and the measurement range image is shown in FIG. 13. A fundus oculi observation screen 400 shown in FIG. 13 includes a tomographic image display 401, a fundus oculi image display 402, a fundus oculi thickness graph display 403, a setting operation part 404, and an information display 405.

A tomographic image G, which is one of tomographic images Gi that were acquired in Step S8, is displayed in the tomographic image display 401. The fundus oculi image Ef' captured by Step 7 is displayed in the fundus oculi image display 402. On the fundus oculi image Ef', a measurement range image R' showing a scanning region R when the tomographic image Gi was acquired is displayed in an overlapping manner. The measurement range image R' and the fundus oculi image Ef' have their display sizes adapted in Step 9.

A cross-sectional position of the tomographic image G displayed in the tomographic image display 401 is represented in a cross-sectional position image T that has been displayed over the fundus oculi image Ef in an overlapping manner.

Fundus oculi thickness graph information RT is displayed in the fundus oculi thickness graph display 403. The fundus oculi thickness graph information RT is a graph in which the distance (or number of pixels from a reference position) in a direction diagonal to the depth-wise direction (z direction) of the fundus oculi Ef is a domain, and the thickness (distance in the depth-wise direction) at a specific location in the fundus oculi Ef in each of the positions in the domain is a codomain (range). The fundus oculi thickness graph information RT may be created, for example, by a method cited in the specification of Japanese Patent Application No. 2006-252953 by the present applicant.

In the setting operation part 404, various kinds of software keys are designed to be used for setting operations related to display modes of the fundus oculi image Ef' or the tomographic image G. In the information display 405, various kinds of information related to an image displayed in the fundus oculi observation screen 400 is displayed. For example, in the information display 405, information related to a patient (patient information) such as patient ID, patient name, patient date of birth, patient gender, etc., or distinction between the right or the left eye E (left eye or right eye), or the scanning method used when the tomographic image Gi is formed) are displayed.

[Actions and Advantageous Effects]

The actions and advantageous effects of the aforementioned fundus oculi observation device 1 will be described.

The fundus oculi observation device 1 is a device capable of acquiring a 2-dimensional image (fundus oculi image Ef') of the surface of the fundus oculi Ef and a tomographic image Gi having a cross-sectional position in a measurement region of the fundus oculi Ef that corresponds to a partial region of the fundus oculi image Ef'. Furthermore, the fundus oculi observation device 1 stores the imaging condition information 213d including the characteristic information such as an axial length representing the characteristic of the eye E and acts so as to display the fundus oculi image Ef' and the measurement range image R' by mutually adapting the display size based on the imaging condition information 213d.

According to the fundus oculi observation device 1, it is possible to represent the positional relationship between an image of the fundus oculi surface and an OCT image with high accuracy, because the fundus oculi image Ef' and the measurement range image R' can be displayed in a state in which the display sizes are matched based on the characteristics of the eye E.

Further, according to the fundus oculi observation device 1 of the present embodiment, because the display size of the fundus oculi image Ef' and the measurement range image R' may be regulated by measuring the axial length of the eye E and using the measurement results, the display size may be adjusted even if the axial length of the eye E was not measured in the past.

Moreover, according to the fundus oculi observation device 1 of the present embodiment, the state of the fundus oculi Ef may be observed in detail, because a tomographic image G may be displayed along with the fundus oculi image Ef' and the measurement range image R'.

[Modification]

The configuration described in detail above is merely an example for favorably implementing the fundus oculi observation device relating to the present invention. Therefore, it is possible to properly apply any modification within the scope of the present invention. Below, various types of modifications will be described.

In the embodiment described above, the reference mirror 174 is placed at a position corresponding to the surface of the fundus oculi Ef to measure the intraocular distance (axial length, etc.) from the entering position of the signal light LS to the reflection position on the surface of the fundus oculi Ef, but it is not limited to this. For example, in the case of placing the reference mirror 174 at a position corresponding to a position at a specific depth from the surface of the fundus oculi Ef, it is possible to measure the intraocular distance between the entering position of the signal light LS and the position at the specific depth by executing the similar process as in the above embodiment.

Figure 14:
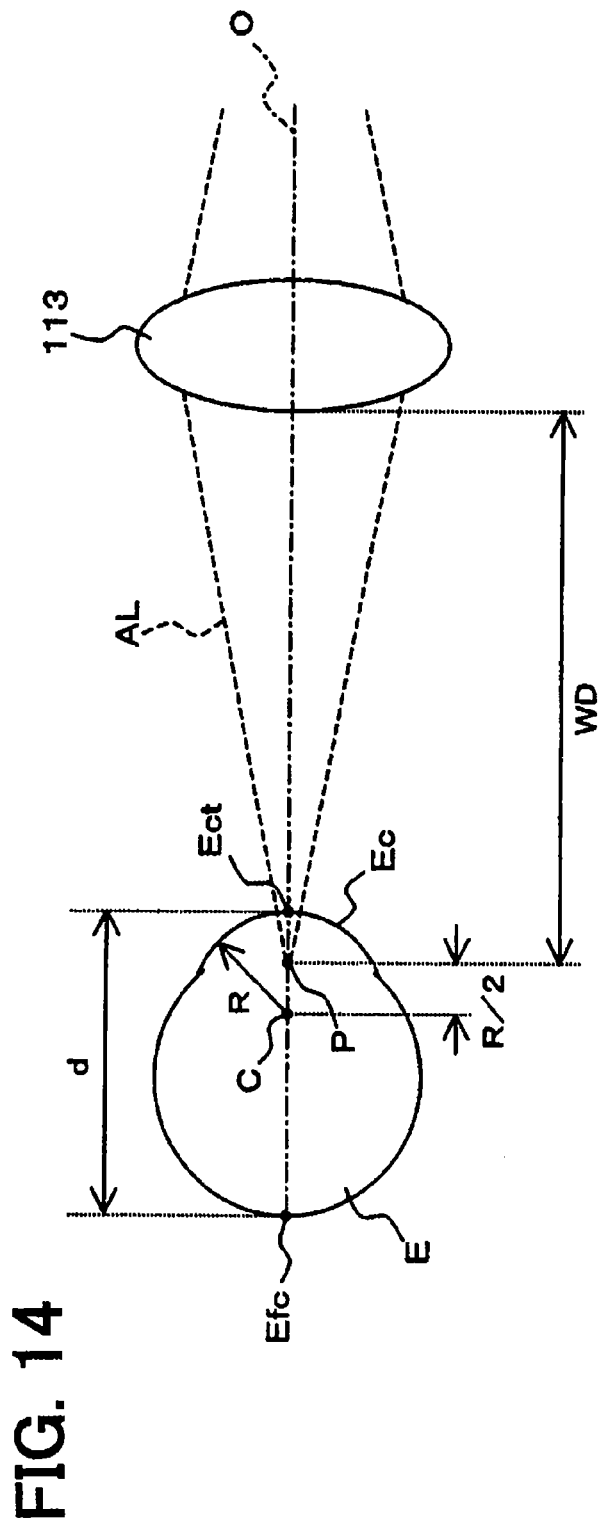
FIG. 14 is a schematic explanatory diagram explaining an operation feature of an intraocular distance in the modification of the preferred embodiment of the fundus oculi observation device according to the present invention.

FIG. 14 shows an example of another measurement pattern of an intraocular distance (axial length) by the fundus oculi observation device according to the present invention. In the case of implementing the measurement pattern shown in the same figure, it is possible to measure by setting a radius of curvature R (as well as a curvature center C) of a cornea Ec of the eye E to an average initial value. Further, the radius of curvature R may be acquired in advance. For example, it is possible to acquire by any device capable of measuring the radius of curvature of a cornea, such as a keratometer. Here, the fundus oculi observation device in the present invention may comprise a component measuring the radius of curvature R. Information of the acquired radius of curvature R (curvature center C) of the cornea Ec is stored in the information storage 213. A symbol O in FIG. 14 denotes an optical axis of the optical system 100, 120.

In the example shown in FIG. 14, at the time of alignment of a device optical system with the eye E by using the alignment optical system 190A, an alignment light (flux) AL is projected to a position P away from the curvature center C of the cornea Ec by one half of the radius of curvature R, not to the surface of the cornea Ec (i.e., the alignment illumination point (alignment target) is projected to this position P). In this case, an actual measurement value WD of the working distance is acquired as a distance between the front position of the objective lens 113 and the position P.

At this moment, among the optical path length $1s$ of the signal light path, the optical path length $1r$ of the reference light path, the actual measurement value WD of the working distance and the axial length d, there is a relationship of $1r=1s+WD+d-R/2$. Therefore, it is possible to obtain the axial length d from the equation of $d=1r-1s-WD+R/2$. In other words, in a case where the intensity of a component corresponding to a part of the signal light LS reflected on the surface of the fundus oculi Ef is the maximum among components contained in detection signals from the CCD 184, the intraocular distance calculator 214 acts to subtract the optical path length $1s$ of the signal light path and the alignment distance WD (actual measurement value of the working distance) from the optical path length $1r$ of the reference light path, respectively, and add a distance of one half of the radius of curvature R to the subtraction result, thereby calculating the axial length d of the eye E.

By executing this process for calculating the axial length, it is possible to measure the axial length with high accuracy in consideration of the projection position of the alignment target.

In general, an intraocular distance (axial length) is an external axial length representing the distance between the corneal vertex (denoted by symbol Ect in FIG. 14) and the eyeball posterior pole (denoted by symbol Efc), and an internal axial length representing the distance between the corneal vertex Ect and the retinal surface of the fovea centralis (not illustrated). In the fundus oculi observation device according to the present invention, it is possible to acquire a tomographic image having a resolving power in the depth direction of a fundus oculi. Therefore, it is possible to acquire information on a sclera for measuring the external axial length, or information on the retinal surface of a fovea centralis for measuring the internal axial length. Moreover, it is possible to acquire information on any layer of the fundus oculi, such as a photoreceptor cell layer and a retinal pigment epithelium layer. Accordingly, at the time of measurement of an intraocular distance (axial length), it is possible to measure the intraocular distance with reference to any layer of a fundus oculi, and it is also possible to measure the intraocular distance with higher accuracy.

For measurement of the intraocular distance (axial length) with reference to an arbitrary layer or position of a fundus oculi, it is possible to provide a designating part for designating the layer or position shown in a 2-dimensional or 3-dimensional fundus oculi image. As the designating part, it is possible to use, for example, a pointing device such as a mouse.

Consequently, it is possible to measure one or both of the external axial length and the internal axial length according to the purpose. Further, it becomes possible to measure an intraocular distance with reference to a designated layer or position with high accuracy. Since it is possible, with the tomographic images of a fundus oculi, to grasp the position of the fovea centralis, it becomes possible to accurately and easily designate the position corresponding to the retinal face of the fovea centralis at the time of measurement of the external axial length or internal axial length used in general.

Further, it is also possible to configure to analyze tomographic images of a fundus oculi and detect the position of a specific (preset) layer of the fundus oculi, thereby obtaining an intraocular distance (axial length) with reference to the layer.

In the example shown in FIG. 14, the alignment is performed with a virtual image acquired when the alignment light flux AL is illuminated at a position away from the curvature center of the cornea by one half of the radius of curvature. However, it is also possible to configure to obtain the radius of curvature R of the cornea Ec by using the corneal reflection light of the alignment light flux AL from a plurality of directions about an optical axis O.

The fundus oculi observation device according to the present invention has a retinal camera (unit) as a device for forming 2-dimensional images of a fundus oculi surface, but it is also possible to configure to form 2-dimensional images of the fundus oculi surface by using an arbitrary fundus oculi observation device such as a slit lamp (slit lamp microscopic device).

In the above embodiment, the process of forming a fundus oculi image is executed by the image forming part 220 (image forming board 208), and various types of control process are executed by the controller 210 (microprocessor 201 or the like). However, it is possible to configure so as to execute both the processes by using one or more computer(s).

In the above embodiment, a fundus oculi observation device comprising a Fourier-domain type of optical image measurement device is described. However, the fundus oculi observation device according to the present invention may comprise an optical image measurement device of another type such as a time-domain type and a swept source type.

[Ophthalmic Image Display Device]

An ophthalmic image display device according to the present invention will be explained. In the above embodiment, the arithmetic and control unit 200 is used as the ophthalmic image display device.

The ophthalmic image display device according to the present invention comprises a display, a storage, and a controller. The display displays a 2-dimensional image (fundus oculi image) of the surface of a fundus oculi of an eye and a tomographic image having a cross-sectional position in a measurement region of the fundus oculi corresponding to a partial region of the 2-dimensional image. The storage stores imaging condition information including characteristic information showing the characteristic of the eye. The controller matches the mutual display sizes of the 2-dimensional image and measurement range image with each other, based on the imaging condition information stored in the storage, and causes the display to display these images.

According to this ophthalmic image display device, it is possible to display the fundus oculi image and the measurement range image in a state in which the display sizes are matched, based on the characteristic of the eye, so that it is possible to present the positional relationship between an image of the fundus oculi surface and an OCT image with high accuracy.

Moreover, the ophthalmic image display device according to the present invention can be configured to display a tomographic image (an OCT image) together with the fundus oculi image and the measurement range image. Consequently, it becomes possible to observe the state of the fundus oculi in detail.

The ophthalmic image display device according to the present invention may comprise any function of the arithmetic and control device 200 of the above embodiment.

A program for controlling the device related to the present invention is now described.

This program is a computer program that causes a computer having a display and a storage to function as the aforementioned ophthalmic image display device (refer to OPHTHALMIC IMAGE DISPLAY DEVICE for the function).

What is claimed is:

1. A fundus oculi observation device comprising:
a first image forming part configured to form a 2-dimensional image of a surface of a fundus oculi of an eye;
a second image forming part configured to form a tomographic image having a cross-sectional position in a measurement region of the fundus oculi corresponding to a partial region of the 2-dimensional image;
a display;
a storage configured to store imaging condition information including characteristic information showing a characteristic of the eye; and
a controller configured to match display sizes of the formed 2-dimensional image and a measurement range image showing a range of the measurement region with each other by changing the display size of at least the formed 2-dimensional image to match the display size of the measurement range image, based on the stored imaging condition information, and cause the display to display the 2-dimensional image and the measurement range image whose display sizes are matched.

2. The fundus oculi observation device according to claim 1, wherein:
the characteristic information includes an axial length of the eye.

3. The fundus oculi observation device according to claim 2, wherein:
the second image forming part includes:
a light source configured to output a low coherence light;
an interference light generator configured to generate an interference light by splitting the outputted low coherence light into a signal light and a reference light and superimposing a fundus oculi reflection light of the signal light applied to the fundus oculi via a signal light path and the reference light reflected by a reference object via a reference light path; and
a detector configured to receive the generated interference light and output a detection signal;
the fundus oculi observation device further comprises an alignment part configured to perform alignment of an optical system forming the signal light path with the eye;
the controller includes an intraocular distance calculator configured to calculate an intraocular distance between a position where the signal light has entered into the eye and a position where the signal light has been reflected by the fundus oculi, based on a light path length of the signal light path, a light path length of the reference light path, a distance between the eye and the optical system when the alignment has been performed, and a detection signal outputted by the detector; and
the storage stores the calculated intraocular distance as the axial length.

4. The fundus oculi observation device according to claim 3, wherein:
the controller causes the display to display a tomographic image formed by the second image forming part together with the 2-dimensional image and the measurement range image whose display sizes have been matched.

5. The fundus oculi observation device according to claim 2, wherein:
the controller causes the display to display a tomographic image formed by the second image forming part together with the 2-dimensional image and the measurement range image whose display sizes have been matched.

6. The fundus oculi observation device according to claim 1, wherein:
the controller causes the display to display a tomographic image formed by the second image forming part together with the 2-dimensional image and the measurement range image whose display sizes have been matched.

7. The fundus oculi observation device according to claim 1, wherein:
the display sizes of the formed 2-dimensional image and the measurement range image are matched by changing the display sizes of both the formed 2-dimensional image and the measurement range image.

* * * * *